(12) United States Patent
Birdno et al.

(10) Patent No.: US 11,541,204 B2
(45) Date of Patent: Jan. 3, 2023

(54) CYCLIC EXPANSION TISSUE TREATMENT PROGRAMS AND ASSOCIATED SYSTEMS

(71) Applicant: W. L. Gore & Associates, Inc., Newark, DE (US)

(72) Inventors: Merrill J. Birdno, Flagstaff, AZ (US); Mike A. Schmieder, Flagstaff, AZ (US); Edward E. Shaw, Flagstaff, AZ (US); Brandon C. Short, Flagstaff, AZ (US); Alireza Mashal, Middleton, WI (US); Matthew B. DeNardo, Melrose, MA (US); Franck J. Rubiconi, Milton Keynes (GB); Linda M. Donoghue, Boston, MA (US); Serge C. Roux, Boston, MA (US)

(73) Assignee: W. L. Gore & Associates, Inc., Newark, DE (US)

( * ) Notice: Subject to any disclaimer, the term of this patent is extended or adjusted under 35 U.S.C. 154(b) by 381 days.

(21) Appl. No.: 16/583,237

(22) Filed: Sep. 25, 2019

(65) Prior Publication Data

US 2020/0094018 A1 Mar. 26, 2020

Related U.S. Application Data

(60) Provisional application No. 62/752,150, filed on Oct. 29, 2018, provisional application No. 62/737,044, filed on Sep. 26, 2018.

(51) Int. Cl.
*A61M 25/10* (2013.01)
*A61M 25/00* (2006.01)
*A61B 17/00* (2006.01)

(52) U.S. Cl.
CPC ... *A61M 25/0023* (2013.01); *A61B 17/00234* (2013.01); *A61M 25/10184* (2013.11);
(Continued)

(58) Field of Classification Search
CPC .... A61M 2025/105; A61M 2025/1086; A61M 25/1018; A61M 25/104
See application file for complete search history.

(56) References Cited

U.S. PATENT DOCUMENTS 4,439,186 A * 3/1984 Kuhl ................... A61M 25/104
604/99.01
5,599,301 A * 2/1997 Jacobs ............ A61M 25/10184
604/65

(Continued)

FOREIGN PATENT DOCUMENTS

EP 0774163 B1 11/2001
JP 2003-000718 A 7/2021
(Continued)

OTHER PUBLICATIONS

International Search Report and Written Opinion received for PCT Patent Application No. PCT/US2019/053251, dated Nov. 22, 2019, 15 pages.
(Continued)

*Primary Examiner* — Deanna K Hall

(57) ABSTRACT

This disclosure relates generally to treatment programs utilizing expansion elements, such as those associated with occlusion and therapeutic agent delivery devices, systems, and methods. In some more specific examples, treatment programs include expansion-contraction cycles at a preselected frequency profile configured to treat a particular condition, such as calcification of an arterial conduit, for example.

24 Claims, 11 Drawing Sheets

(52) U.S. Cl.
CPC .............. *A61B 2017/00292* (2013.01); *A61M 2025/0024* (2013.01); *A61M 2025/105* (2013.01)

(56) References Cited

U.S. PATENT DOCUMENTS

| | | |
|---|---|---|
| 5,708,044 A | 1/1998 | Branca |
| 5,752,934 A | 5/1998 | Campbell et al. |
| 6,541,589 B1 | 4/2003 | Baillie |
| 7,531,611 B2 | 5/2009 | Sabol et al. |
| 8,637,144 B2 | 1/2014 | Ford |
| 8,937,105 B2 | 1/2015 | Xu et al. |
| 10,279,084 B2 | 5/2019 | Goepfrich et al. |
| 2013/0116655 A1 | 5/2013 | Bacino et al. |
| 2014/0172066 A1 | 6/2014 | Goepfrich et al. |
| 2016/0143579 A1 | 5/2016 | Martikka et al. |
| 2018/0153568 A1 | 6/2018 | Kat-Kuoy |

FOREIGN PATENT DOCUMENTS

| | | |
|---|---|---|
| WO | 2014/022867 A1 | 2/2014 |
| WO | 2016/134225 A1 | 8/2016 |
| WO | 2016/138260 A1 | 9/2016 |
| WO | 2017/168145 A1 | 10/2017 |

OTHER PUBLICATIONS

U.S. Provisional Application filed on Apr. 24, 2018, by Bohn et al., Entitled, "Balloon Catheters, Systems and Methods", U.S. Appl. No. 62/661,942.

* cited by examiner

CYCLIC EXPANSION TISSUE TREATMENT PROGRAMS AND ASSOCIATED SYSTEMS

CROSS-REFERENCE TO RELATED APPLICATION

This application claims the benefit of Provisional Application No. 62/752,150, filed Oct. 29, 2018, and also claims the benefit of Provisional Application No. 62/737,044, filed Sep. 26, 2018, both of which are incorporated herein by reference in their entireties for all purposes.

FIELD

This disclosure relates generally to treatment programs utilizing expansion elements, such as those associated with occlusion and therapeutic agent delivery devices, systems, and methods. In some more specific examples, the disclosure provides for expansion-contraction cycles at a preselected frequency profile configured to treat a particular condition, such as calcification of an arterial conduit, for example.

BACKGROUND

A variety of diseases and physical ailments or conditions may benefit from interventions using an expansion element engaged with tissue at a treatment site. Vascular diseases, such as arthrosclerosis, artery occlusion, vascular prophylactic intervention, phlebitis, intimal hyperplasia, plaques, vascular dissections, peripheral artery disease, aneurismal disease, stenosis, restenosis, and skin expansion, are just a few examples of diseases/treatments that may benefit from an intervention including use of an expansion element, such as a catheter balloon, for actively engaging tissue. Improvements in tissue response, including vascoelastic response in association with such treatments remain to be realized.

International Pub. No. WO 2017/168145 relates to a medical device for assisting the break-up, disruption or disintegration of calcified or other hardened material within vessels of the human or animal body which material otherwise prevents or inhibits stenting procedures or passage of guidewires, catheters and other devices through the vessels. The device comprises a catheter having a lumen extending between a distal end and a proximal end of the catheter and a displaceable element at the distal end of the catheter configured for axial and/or radial displacement relative to the catheter when driven by pressure fluctuations within the lumen. A pressure pump is coupled to a proximal end of the catheter and is configured for application of a baseline pressure to the catheter lumen. A pressure modulation source is also coupled to the proximal end of the catheter, configured to modulate the baseline pressure in the catheter lumen with one or more pressure impulses, and preferably with a series of pressure pulses.

International Pub. No. WO 2016/134225 relates to a system directed to rotational atherectomy systems and methods generally. More specifically, a method for methodically softening and otherwise disrupting calcification located within atherosclerotic plaque, lesion or occlusion and/or within the wall of a biological conduit or lumen. The softening and/or disruption of the calcification in the walls of the exemplary artery is accomplished in conjunction with abrading removal of any occlusion located on the interior surface of the exemplary artery and, therefore, located within the artery's lumen. This result is achieved by use of at least one eccentric head that, during high-speed rotation within the exemplary lumen, has been found to produce a combination of a low-frequency orbital motion comprising a force that is exerted against the lumen wall, with concomitant deflection of same, and/or a high-frequency pulsatile frequency, also with concomitant exertion of force against the lumen wall and deflection of same.

U.S. Pat. No. 4,439,186 relates to a dilation device for dilating or blocking vessels and other body cavities with a catheter having an expansion element. The expansion element is a balloon-type dilation element having a pressure volume relationship which is non-linear. A pressure source is provided which supplies a pulsating pressure to the expansion element for alternating expansion and contraction of said element.

EP 0 774 163 relates to a stent expansion system that comprises a balloon catheter, which has a portion of its tubular shaft sequentially squeezed between a ram reciprocating in a box and a saddle arranged in a cover closely fitting on the box. The pressurized fluid medium supplied to the balloon is pulsated by the squeeze and release action of the ram and saddle arrangement.

Improvements to tissue response to expansion treatment remain to be realized. None of the foregoing is believed to effectively address a preselected cyclic treatment profile including that emulate or otherwise leverage complex elastic material (e.g., stress relaxation) response like that ascribed to the Mullins effect, which is a particular aspect of the mechanical response in filled rubbers.

SUMMARY

Various inventive aspects described herein relate to systems, methods, and associated expandable, intraluminal devices (e.g., balloons) for achieving improved tissue response to dilation or other tissue expansion procedures. For example, various concepts are provided by this disclosure that relate to cyclical strain profiles used with expandable, intraluminal devices for achieving improved histological response. Although primary examples are provided in the context of blood vessel treatments (e.g., balloon catheter operations on calcified vessels), it should be understood that the term "intraluminal" and the applicability of the described methodologies and associated systems apply in a variety of contexts, including without limitation treatment of the following: peripheral arterial disease, arteriovenous fistula, venous disease, kyphoplasty, sinuplasty, skin expansion, valve disease (e.g., calcification), or others.

In some examples, the above referenced systems and methods leverage concepts associated with the Mullin's effect, which describes a type of hysteresis that applies to complex rubber material, where the strain-curve of a particular material depends on the maximum loading previously encountered by that material. Various inventive concepts of the instant disclosure leverage the theory that a similar mechanism as Mullin's effect translates to certain types of tissues, including diseased tissue, which may be leveraged to achieve tissue softening/relaxation utilizing the existence of residual strain/elongation after an expansion cycle and/or enhanced treatment for breaking up, disrupting, or disintegrating calcified or other hardened material within vessels of the human or animal body.

A first example ("Example 1") relates to a method of treating a vessel having a nominal (starting) diameter at a treatment site in a mammalian body in which the method includes providing an apparatus that includes an expansion element mounted on a catheter, the expansion element configured to enlarge and contract at a first frequency of 0.1 to 10 Hz. The method also includes orienting the expansion element at the treatment site and cycling the expansion element at the treatment site at the first frequency between a first diameter that is greater than the nominal (starting diameter) and a second diameter that is less than the first diameter. According to the method, the nominal (starting) diameter of the treatment site is increased following the treatment and removal of the expansion element.

According to another example further to Example 1 ("Example 2"), the expansion element is a drug coated balloon and one or more of the following occurs as a result of the treatment: drug uptake increase at the treatment site, drug loss decrease at the treatment site, total drug volume required for treatment is decreased at the treatment site, drug transfer efficiency from the drug coated balloon is increased at the treatment site, and/or drug wash off from the treatment site is reduced.

According to another example further to any preceding Example ("Example 3"), the expansion element is cycled according to a frequency configured to treat any one or more of the following: specific vessels, vessel disease states in below-the-knee vessels, vessel disease states in above-the-knee vessels, arterial venous circuits, coronary vessels, medial and/or luminal calcified lesions and/or vessels, venous valve disease, Kyphoplasty, and fistula maturation (AV Circuit).

According to another example further to any preceding Example ("Example 4"), the expansion element is cycled according to a treatment program in which one or more of the following is varied: strain rate, strain percentages, number of cycles, expansion amplitude, expansion frequency, change in expansion element volume, change in expansion element pressure, and change in expansion element diameter.

According to another example further to any preceding Example ("Example 5"), the expansion element has a compliance configured to treat a desired vessel diameter.

According to another example further to any preceding Example ("Example 6"), the expansion element is configured to radially expand with an absence of localized shear loading on the vessel.

According to another example further to any preceding Example ("Example 7"), the expansion element is longitudinally flexible.

According to another example further to any preceding Example ("Example 8"), the expansion element includes any one or more of the following features: drug coating, scoring elements, cutting elements, topographic features, and a scaffold attached to a balloon.

According to another example further to any preceding Example ("Example 9"), the expansion element is cycled at the first frequency using one or more of the following: a hand held battery-operated catheter system, a squeeze bulb, a piston pump, a screw drive, and an air modulator.

Another example ("Example 10") relates to a method of treating a tissue site in a body of a patient, the tissue site having a nominal size, the method including delivering one or more expansion elements of a medical device to the tissue site, the medical device being configured to expand and contract the one or more expansion elements. The method also includes operating the medical device according to a treatment program such that the one or more expansion elements are expanded and contracted at a treatment frequency having a value from 0.1 Hz to 10 Hz, the one or more expansion elements being expanded and contracted between a first size and a second size that is greater than the first size through a graduating, cyclic expansion profile including the second size graduating in value from an initial value that is greater than the nominal size and a subsequent value that is greater than the initial value. The method also includes removing the one or more expansion elements from the tissue site, whereby the nominal size of the tissue site is increased following removal of the one or more expansion elements.

According to another example further to Example 10 ("Example 11"), the one or more expansion elements include an intraluminal balloon.

According to another example further to any one of Examples 10 or 11 ("Example 12"), wherein the tissue site is one of a blood vessel, a heart valve, or a respiratory conduit.

According to another example further to any one of Examples 10 to 12 ("Example 13"), the treatment frequency is varied during the treatment program.

According to another example further to any one of Examples 10 to 12 ("Example 14"), the treatment frequency is constant during the treatment program.

According to another example further to any one of Examples 10 to 14 ("Example 15"), the treatment program is carried out using a single expansion element.

According to another example further to any one of Examples 10 to 14 ("Example 16"), the treatment program is carried out using a plurality of expansion elements, the method further comprising using a first expansion element of the plurality of expansion elements to carry out a first portion of the treatment program and a second expansion element of the plurality of expansion elements to carry out a second portion of the treatment program, the first expansion element having a first nominal expansion size and the second expansion element having a second nominal expansion size.

According to another example further to any one of Examples 10 to 16 ("Example 17"), the treatment program includes varying one or more of a volume, a pressure, and a diameter of the one or more expansion elements during the treatment program.

According to another example further to any one of Examples 10 to 17 ("Example 18"), the treatment program is configured to carry out, and the method is associated with one of a sinuplasty, kyphoplasty, rhinoplasty, or a skin expansion procedure.

According to another example further to any one of Examples 10 to 18 ("Example 19"), the one or more expansion elements include a compliant balloon.

According to another example further to any one of Examples 10 to 19 ("Example 20"), wherein the one or more expansion elements include a non-compliant balloon.

According to another example further to any one of Examples 10 to 20 ("Example 21"), the medical device is coupled to a pressure modulator that includes a power source connected to a pressurizing source and a controller for controlling the pressurizing source, the pressurizing source being coupled with the one or more expansion elements for pressurizing and de-pressurizing the one or more expansion elements and the controller including a processor for causing the pressurizing source to operate the one or more expansion elements according to the treatment program.

According to another example further to Example 21 ("Example 22"), the power source, the pressurizing source, and the controller are maintained in a housing.

According to another example further to Example 22, the housing is configured to be held in a hand of a user.

According to another example further to any one of Examples 10 to 23 ("Example 24"), the pressure modulator includes a pressurizing source that includes one or more of a piston drive, a screw drive, an air compressor, a gas cartridge, a servo motor, a piezo electric motor, and/or a pressurized fluid reservoir.

According to another example further to any one of Examples 10 to 24 ("Example 25"), the expansion element includes one or more of scoring features, drug coating, cutting features, controlled topography features, and/or off axis expansion features.

The foregoing Examples are just that, and should not be read to limit or otherwise narrow the scope of any of the inventive concepts otherwise provided by the instant disclosure. While multiple examples are disclosed, still other embodiments will become apparent to those skilled in the art from the following detailed description, which shows and describes illustrative examples. Accordingly, the drawings and detailed description are to be regarded as illustrative in nature rather than restrictive in nature.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

Figure 1:
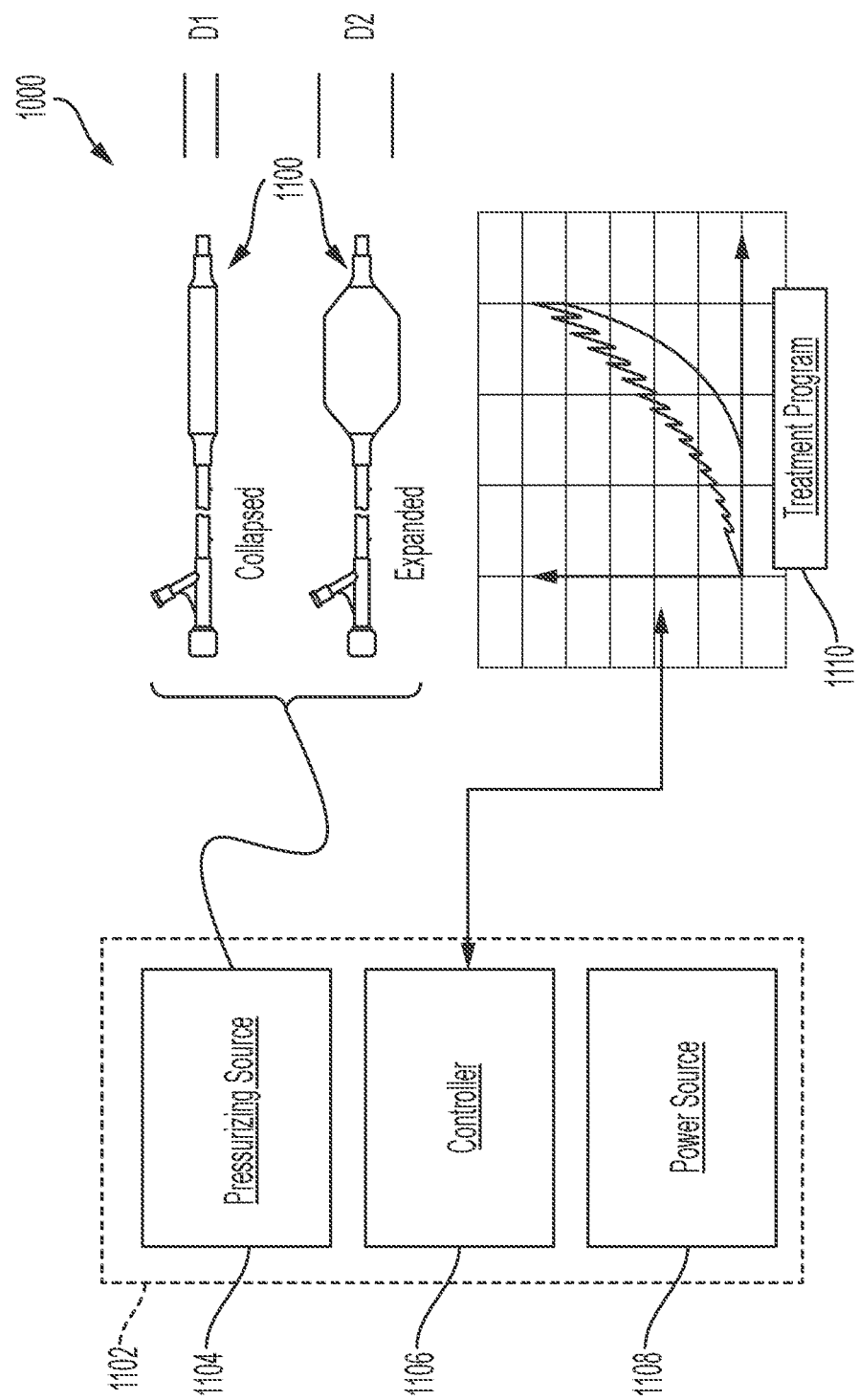
FIG. 1 shows a system for treating a tissue site in a body of a patient, according to some examples.

Persons skilled in the art will readily appreciate that various aspects of the present disclosure can be realized by any number of methods and apparatus configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

DETAILED DESCRIPTION

Some inventive concepts provided by this disclosure relate to predetermined, cyclical (e.g., low-frequency) expansion-contraction treatment programs and associated systems for tissue treatment. In some examples, such treatment programs and associated systems include catheter-based balloon treatment of calcified plaque that leverage concepts analogous to that of the Mullins effect exhibited in filled rubber materials. The inventors have confirmed the basis for such theories utilizing, among other tools, finite element model (FEM) analysis and cadaver vessel response testing indicating that such treatment programs can lead to more effective stress transmission to diseased tissue (e.g., calcified region) and improved treatment capability through tissue softening/relaxation response. Such stress transmission may assist with enhanced treatment for breaking up, disrupting, or disintegrating calcified or other hardened material within vessels of the human or animal body, for example, or provide other treatments as desired.

This disclosure is not meant to be read in a restrictive manner. For example, the terminology used in the application should be read broadly in the context of the meaning those in the field would attribute such terminology.

With respect to terminology of inexactitude, the terms "about" and "approximately" may be used, interchangeably, to refer to a measurement that includes the stated measurement and that also includes any measurements that are reasonably close to the stated measurement. Measurements that are reasonably close to the stated measurement deviate from the stated measurement by a reasonably small amount as understood and readily ascertained by individuals having ordinary skill in the relevant arts. Such deviations may be attributable to measurement error or minor adjustments made to optimize performance, for example. In the event it is determined that individuals having ordinary skill in the relevant arts would not readily ascertain values for such reasonably small differences, the terms "about" and "approximately" can be understood to mean plus or minus 10% of the stated value.

Certain terminology is used herein for convenience only. For example, words such as "top", "bottom", "upper," "lower," "left," "right," "horizontal," "vertical," "upward," and "downward" merely describe the configuration shown in the figures or the orientation of a part in the installed position. Indeed, the referenced components may be oriented in any direction. Similarly, throughout this disclosure, where a process or method is shown or described, the method may be performed in any order or simultaneously, unless it is clear from the context that the method depends on certain actions being performed first.

Examples of Automated Systems

FIG. 1 shows a system 1000 for treating a tissue site in a body of a patient, according to some examples. As shown schematically in FIG. 1, the system 1000 includes a medical device 1100 and a pressure modulator 1102 connected to the medical device 1100. As shown, the pressure modulator 1102 includes a pressurization source 1104, a controller 1106, and a power source 1108. In some examples, the pressure modulator 1102 is automated, or partially automated, and the power source 1108 is electrical (e.g., a battery), the controller 1106 is electronic (e.g., a microprocessor-based system), and the pressurizing source 1108 is actuated by the controller 1106 according to a treatment program 1110. As shown in FIG. 1, the medical device 1100 is transitionable between collapsed and expanded states or sizes. In some examples, the pressure modulator 1102 or portions thereof are contained in a hand-held housing unit. In other examples, the pressure modulator 1102 or portions thereof are maintained by a suitable portable or stationary housing as appropriate (see, e.g., FIGS. 5A and 5B).

Some methods of treating a vessel having a nominal (starting) diameter at a treatment site in a mammalian body include providing an apparatus such as that described above (e.g., one which includes an expansion element) mounted on a catheter, such as the medical device 1100. The expansion element is configured to enlarge and contract according to a treatment program at a first frequency (e.g., 0.1 to 10 Hz). In some examples, the expansion element is oriented at the treatment site and cycled at the first frequency to a first diameter greater than the nominal (starting) diameter of the treatment site and then to a second diameter that is less than the first diameter (e.g., greater than the nominal (starting)

diameter, the same as the nominal (starting) diameter, or less then the nominal (starting) diameter of the treatment site). In such a manner, the nominal (starting) diameter of the treatment site is increased following the treatment program and removal of the expansion element.

In some examples, a method of treating a tissue site (e.g., a vessel) in a body of a patient, the tissue site having a nominal size, includes delivering one or more expansion elements of the medical device 1100 to a tissue site, the medical device 1100 being configured to expand and contract the one or more expansion elements. The medical device 1100 is operated according to a treatment program such that the one or more expansion elements are expanded and contracted at a treatment frequency having a desired value (e.g., from 0.1 Hz to 10 Hz), the one or more expansion elements being expanded and contracted between a first size and a second size (that is greater than the first size) through a graduating, cyclic expansion profile. In some examples, the cyclic expansion program includes the second size of the one or more expansion elements graduating in value from an initial value that is greater than the nominal size of the tissue site and a subsequent value that is greater than the initial value. In some methods, the one or more expansion elements are removed from the tissue site, whereby the nominal size of the tissue site is increased following removal of the one or more expansion elements.

Examples of Manual Systems/Operation

In various examples, a user (not shown) actuates one or more medical devices and/or pressure modulation systems according to the treatment program using manual techniques (e.g., by hand operated pressurizing systems). As one non-limiting example, a physician may select to operate a syringe or other pressurizing system in a manual manner to selectively cycle one or more expansion elements at a desired frequency according to a treatment program as described herein.

Examples of Medical Device Features

Figure 2:
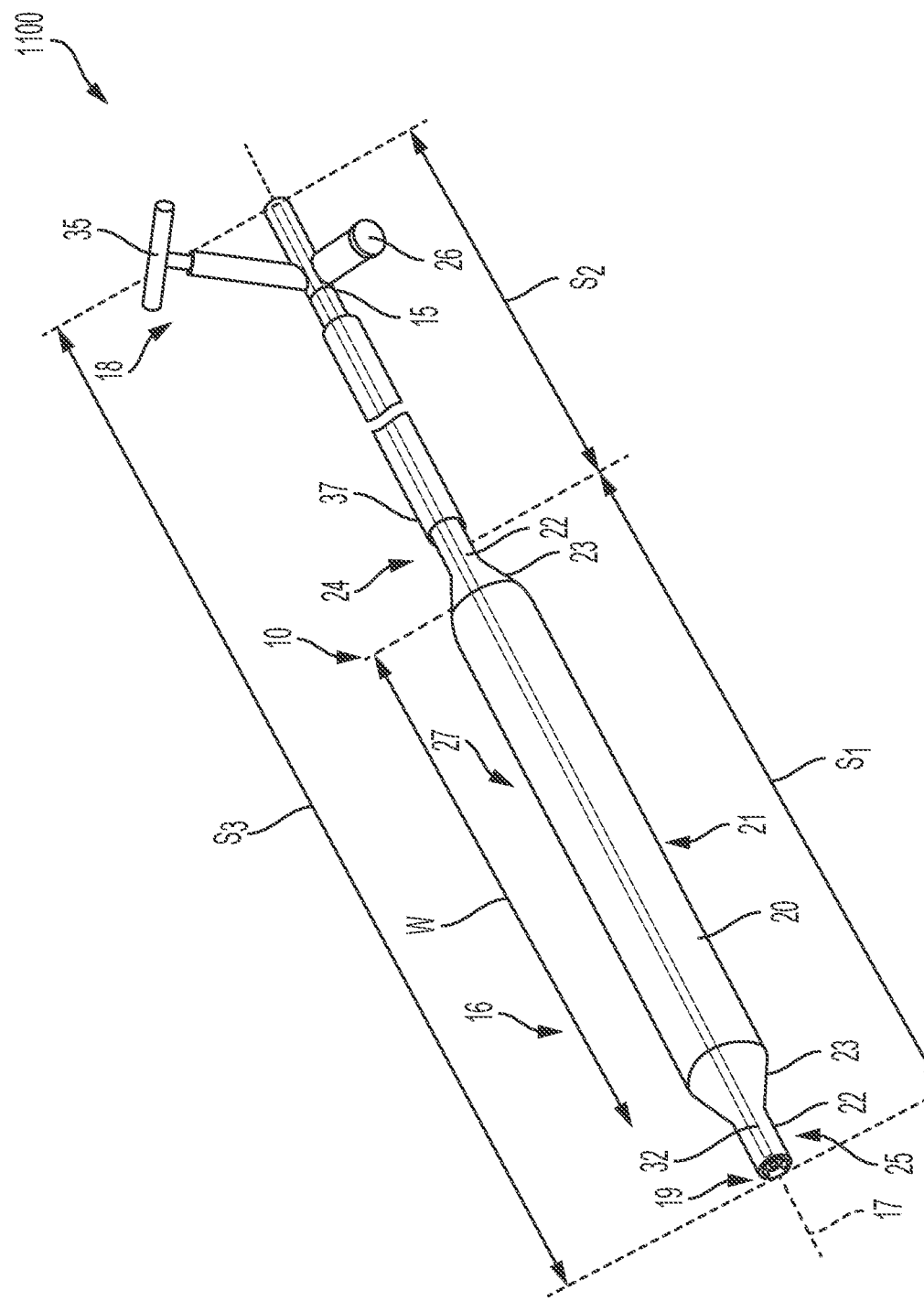
FIG. 2 shows a medical device of the system of FIG. 1 for treating tissue in a body of a patient, according to some examples.

FIG. 2 shows the medical device 1100 for treating tissue in a body of a patient, according to some examples. As shown, the medical device 1100 includes an expansion element 10 and a catheter 15. In various embodiments, the catheter 15 has a cylindrical form and comprises a longitudinal axis 17, a proximal end 18, a distal end 19, and a cover lumen 32 optionally extending from the proximal end 18 to the distal end 19. The expansion element 10 comprises an inflatable member or expandable member 20 positioned on a distal section 16 of the catheter 15. As shown, the expandable member 20 includes a body section 21 that may be substantially cylindrical along a working length (W), two opposed leg portions 22, and shoulder/tapered portions 23 that may be integrally connected to the body section 21 and the two opposed leg portions 22. The body section 21, the leg portions 22, and the shoulder/tapered portions 23 define an overall length of the expandable member 20 from a proximal end 24 to a distal end 25.

The medical device 1100 has a first section $S_1$ that extends from a distal end 19 of the catheter 15 to the proximal end 24 of the expandable member 20. The medical device 1100 also has a second section $S_2$ that extends from the proximal end 24 of the expandable member 20 to the proximal end 18 of the catheter 15. The medical device 1100 also has a third section $S_3$ that corresponds to a length of the catheter 15 that extends from the distal end 19 of the catheter 15 to the proximal end 18 of the catheter 15 within the cover lumen 32 of the catheter 15.

Examples of Expansion Element Features

In some embodiments, the expandable member 20 of the expansion element 10 comprises a thermoplastic polymeric material that includes urethanes, PET, PEBAX, polytetrafluoroethylene (PTFE), polyamides such as nylon 12, nylon 11, nylon 9, nylon 6/9, nylon 6/6, and combinations thereof.

The expandable member 20 of the expansion element 10 can include, for example, a non-compliant, generally inelastic balloon. In such examples, the expandable member 20 can include a material that is configured to allow the expandable member 20 to expand to a chosen diameter upon sufficient pressurization and remain at or near the chosen diameter under further pressurization until a burst pressure is reached, such as, for example, nylon, polyethylene, polyethylene terephthalate (PET), polycaprolactam, polyesters, polyethers, polyamides, polyurethanes, polyimides, ABS copolymers, polyester/polyether block copolymers, ionomer resins, liquid crystal polymers and rigid rod polymers.

In some examples, the expandable member 20 can include a compliant, relatively elastic balloon. In such examples, the expandable member 20 can include a material that is configured to allow the balloon to continuously increase in diameter as pressure to the expandable member 20 is increased, such as, for example polyurethanes, latex and elastomeric organosilicone polymers, such as, polysiloxanes. A compliant, relatively elastic expandable member 20 may be preferable for deployment around a curve, such as within a vasculature of a patient as a more elastic expandable member 20 may mitigate undesirable straightening force during deployment. However, as compared to a non-compliant, generally inelastic expandable member 20, a compliant, relatively elastic expandable member 20 may be more susceptible to uneven deployment.

In yet other examples, the expandable member 20 includes a semi-compliant balloon. In such examples, the expandable member 20 incorporates both compliant and non-compliant attributes in one or more portions (e.g., layers, sections, or segments) of material. Additionally, a base layer (or layers) of a balloon may be characterized by a first compliance while a cover layer (or layers) of a balloon may have a second, different compliance. Although described in connection with compliant and non-compliant examples, any material or configuration that allows the expandable member 20 to inflate in a predictable manner within the body of a patient, including in a combination of compliant and non-compliant behavior, is within the scope of the present disclosure. Examples of balloons providing low straightening forces are disclosed in United States Patent Publication Number 2014/0276406, titled, "Conformable balloon devices and methods," and may also be suitable for use as the expandable member 20 according to various embodiments.

The working length (W) of the expandable member 20 may be from about 10 mm to about 400 mm, from about 10 mm to about 250 mm, or from about 10 mm to 150 mm. Similarly, the nominal diameter of the expandable member 20 can be from about 1 mm to about 100 mm, from about 1 mm to about 60 mm, or from about 2 mm to about 30 mm. By way of example, the expandable member 20 can have a nominal diameter from about 2 mm to about 10 mm and a working length (W) from about 10 mm to about 200 mm, or a nominal diameter from about 6 mm to about 25 mm and working length (W) from about 15 mm to about 150 mm. As should be understood, the expandable member 20 may have any appropriate dimension and size for any appropriate clinical application as desired.

In various embodiments, the expandable member 20 is attached or mounted to the catheter 15 at the leg portions 22 such that the catheter 15 is in fluid communication with the expandable member 20. For example, the catheter 15 may comprise one or more lumens, one of which may be in fluid communication, optionally through an orifice in the catheter, with a chamber of the expandable member 20 for supplying inflation fluid to inflate the expandable member 20 in a tubular structure such as a patient's vasculature.

In some examples, the expansion element 10 also further comprises a cover 27, such as that described in Applicant's application Ser. No. 15/711,189, filed Sep. 21, 2017 or Applicant's application Ser. No. 14/132,767 filed Dec. 18, 2013 and published as US 2014/0172066.

For example, in some embodiments the cover 27 comprises a porous layer, for example but not limited to a porous fluoropolymer layer. In accordance with certain embodiments, the porous fluoropolymer layer may include, without limitation, perfluoroelastomers and the like, polytetrafluoroethylene (PTFE) and the like, and expanded fluoropolymers and the like. Non-limiting examples of expandable fluoropolymers include ePTFE, expanded modified polytetrafluoroethylene, and expanded copolymers of polytetrafluoroethylene. For example, an extruded ePTFE tube, a helical wrapped ePTFE tube, or a cigarette wrapped ePTFE tube.

Various expandable blends of PTFE, expandable modified PTFE, and expanded copolymers of PTFE are disclosed in the art, such as in U.S. Pat. No. 5,708,044 to Branca; U.S. Pat. No. 6,541,589 to Baillie; U.S. Pat. No. 7,531,611 to Sabol et al.; U.S. Pat. No. 8,637,144 to Ford; and U.S. Pat. No. 8,937,105, to Xu et al. U.S. Publication No. US20160143579 discloses additional embodiments as well as methods of making embodiments suitable for use herein.

In accordance with various embodiments, a plurality of regions of the cover 27 (e.g., first, second, and third regions) distributed along the first section 51 and second section S2 of the medical device 1100 are configured to move longitudinally in the distal direction over the expandable member 20 throughout deployment of the expansion element 10 within a tubular structure of a patient such that repeated inflations of the expandable member 20 may result in different regions of the cover 27 applying multiple treatments or functional surfaces to the tubular structure, without removal of the element 10 from a body lumen in which it is positioned.

In some embodiments where the cover 27 comprises a porous layer, one or more coatings may be applied to the porous layer. The one or more coatings may include therapeutic agents that may be applied to a region of the cover 27 such that a therapeutic agent coating substantially covers the working length (W) of the expandable member 20. Alternatively, the one or more therapeutic agent coatings may be applied to a portion of the cover 27 such that a therapeutic agent coating substantially covers the working length (W) of the expandable member 20 and is disposed on at least a region of the opposed leg regions 22 and/or shoulder/tapered regions 23. The same therapeutic agent coating may be disposed on one or more regions of the cover 27, one or more different therapeutic agent coatings may be disposed on one or more regions of the cover 27, no coating may be disposed on one or more regions of the cover 27, and/or a therapeutic agent coating may include one or more radiopaque elements, as described in further detail herein.

Figure 3:
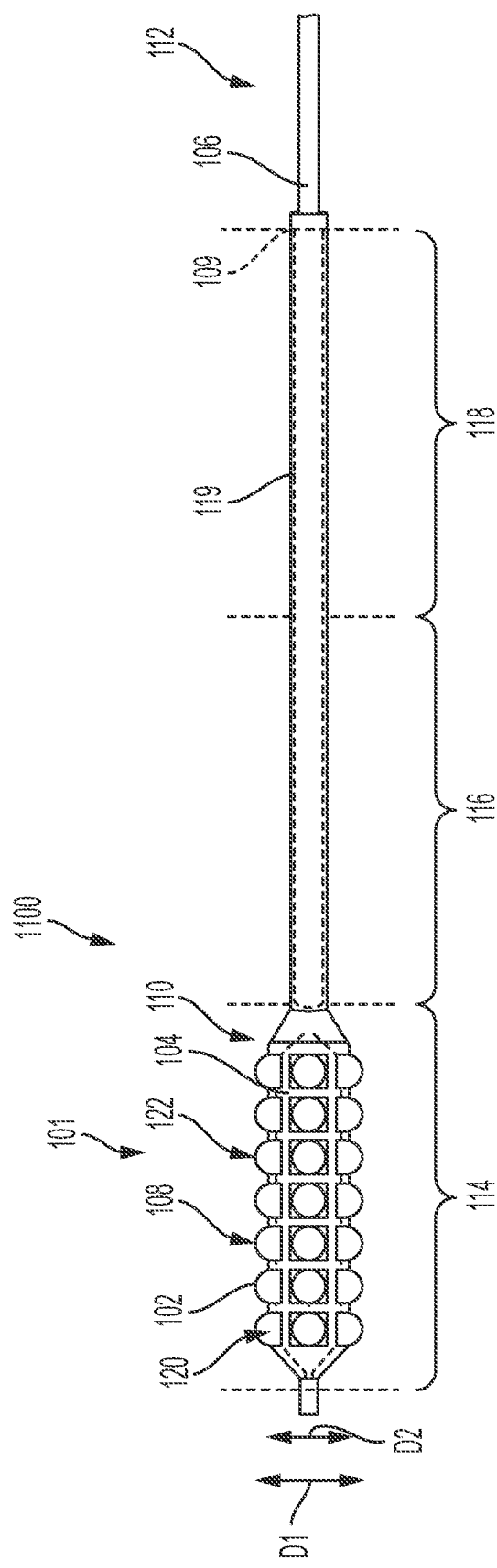
FIG. 3 shows an expansion element of the medical device of the system of FIG. 1, according to some examples.
Figure 4:
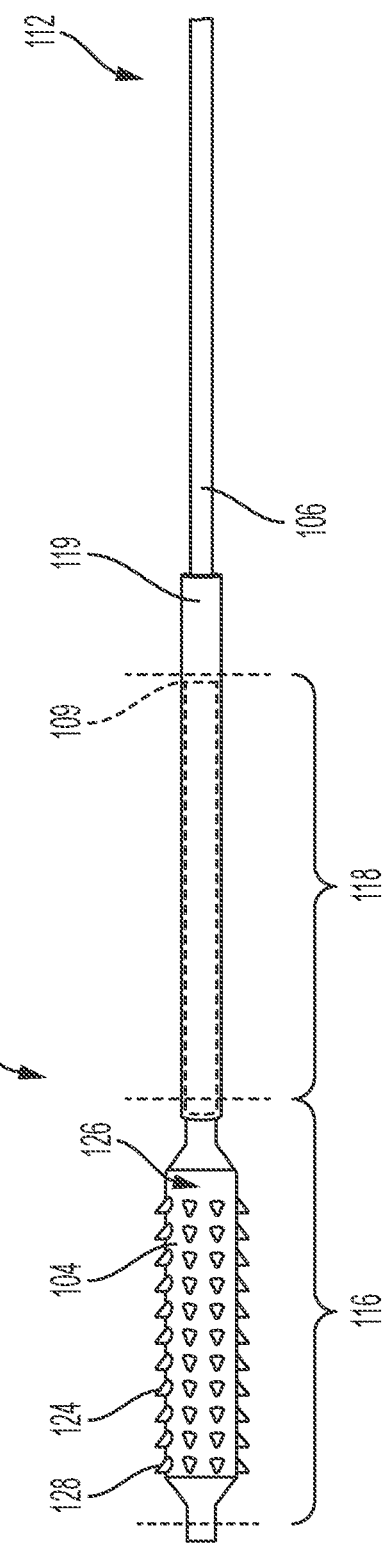
FIG. 4 shows an expansion element of the medical device of the system of FIG. 1, according to some examples.

In some embodiments, the outer surface of the cover 27 and/or the expandable member 20 may have a surface texture and/or surface feature (see, e.g., FIGS. 3 and 4). The surface texture and/or surface feature may be part of a region of the cover 27 and/or the expandable member 20 such that the surface texture and/or surface feature extends along the working length (W) of the expandable member 20. Alternatively, the surface texture and/or surface feature may be part of a region of the cover 27 and/or the expandable member 20 such that the surface texture and/or surface feature extends along the working length (W) of the expandable member 20 and is disposed on at least a portion of the opposed leg portions 22 and/or shoulder/tapered portions 23. The same surface texture and/or surface feature may be disposed on one or more regions of the cover 27, one or more surface texture and/or surface feature may be disposed on one or more regions of the cover 27, no surface texture and/or surface feature may be disposed on one or more regions of the cover 27, and/or a surface texture and/or surface feature may include one or more radiopaque elements, as described in further detail herein.

The expansion element 10 may further comprise a cylindrical sheath 37 disposed along at least a portion of the second section S2 of the medical device 1100 about a portion of the cover 27. In some embodiments, the sheath 37 wraps around the entire circumference of the cover 27 and covers an entire length of the cover 27 disposed along the second section S2 of the medical device 1100. In other embodiments, the sheath 37 wraps around a portion of the circumference of the cover 27 and/or covers a portion of the cover 27 disposed along the second section S2 of the medical device 1100. The sheath 37 may protect a therapeutic agent coating (e.g., a drug coating or a densified coating) on an outer surface of the cover 27 positioned beneath the sheath 37 during placement of the expansion element 10 in the tubular structure of a patient. The sheath 37 may also retain a portion of the cover 27 positioned beneath the sheath 37 at a delivery diameter during the use of the expansion element 10. In some embodiments, the sheath 37 is bonded to a region of the catheter 15 by an adhesive. For example, the sheath 37 may be bonded to a handle or hub at the proximal end 18 of the catheter 15. In other embodiments, the sheath 37 is not bonded to the catheter 15.

In various embodiments, the sheath 37 may comprise a polymer tube or a tube comprising other suitable materials, including but not limited to thermoplastics, for example but not limited to Polymethyl Methacrylate (PMMA or Acrylic), Polystyrene (PS), Acrylonitrile Butadiene Styrene (ABS), Polyvinyl Chloride (PVC), Modified Polyethylene Terephthalate Glycol (PETG), Cellulose Acetate Butyrate (CAB); Semi-Crystalline Commodity Plastics that include Polyethylene (PE), High Density Polyethylene (HDPE), Low Density Polyethylene (LDPE or LLDPE), Polypropylene (PP), Polymethylpentene (PMP); Polycarbonate (PC), Polyphenylene Oxide (PPO), Modified Polyphenylene Oxide (Mod PPO), Polyphenylene Ether (PPE), Modified Polyphenylene Ether (Mod PPE), Thermoplastic Polyurethane (TPU); Polyamides such as nylon-11 and nylon-12, Polyoxymethylene (POM or Acetal), Polyethylene Terephthalate (PET, Thermoplastic Polyester), Polybutylene Terephthalate (PBT, Thermoplastic Polyester), Polyimide (PI, Imidized Plastic), Polyamide Imide (PAI, Imidized Plastic), Polybenzimidazole (PBI, Imidized Plastic); Polysulfone (PSU), Polyetherimide (PEI), Polyether Sulfone (PES), Polyaryl Sulfone (PAS); Polyphenylene Sulfide (PPS), Polyetheretherketone (PEEK); Fluoropolymers that include Fluorinated Ethylene Propylene (FEP), Ethylene Chlorotrifluoroethylene (ECTFE), Ethylene, Ethylene Tetrafluoroethylene (ETFE), Polychlortrifluoroethylene (PCTFE), Polyvinylidene Fluoride (PVDF), Perfluoroalkoxy (PFA), or combinations, copolymers, or derivatives thereof. Other commonly known medical grade materials include elastomeric organosilicon polymers, polyether block amide (e.g., PEBAX®). In particular, polyamides can include nylon 12, nylon 11, nylon 9, nylon 6/9, and nylon 6/6. In certain embodiments, PET, nylon, and PE may be selected for medical balloons used in coronary angioplasty or other high-pressure applications. The specific choice of materials depends on the desired characteristics/intended application of the balloon.

FIGS. 3 and 4 show additional or alternative features for the expansion element 10 of the medical device 1100. FIG. 3 shows another expansion element 101 of the medical device 1100 positioned on a catheter 106, according to some embodiments. The expansion element 101 optionally includes similar features to those described in association with the expansion element 10 as additional or alternative features of the expansion element 101 and vice versa.

A shown, the expansion element 101 includes an inflatable member or expandable member 102. As shown in FIG. 3, the first region 114 of the cover 104 can comprise at least one aperture 120. The first region 114 of the cover 104 can constrain a region of expandable member 102 during inflation. The restraining action of first region 114 of the cover 104 causes expandable member 102 to distend at apertures 120 in the first region 114 of the cover 104. As shown in FIG. 3, the portions of the expandable member 102 distending through the apertures 120 of the first region 114 of the cover 104 has a diameter shown as "D1." The first region 114 of the cover 104 positioned over the expandable member 102 has a diameter of "D2," as shown in FIG. 3. Apertures 120 can comprise an opening or weakened site in the first region 114 of the cover 104. In this regard, an opening can be a hole, cut, or any other discontinuous section of the material of the first region 114 of the cover 104. For example, a hole could be formed by puncturing first region 114 of the cover 104. Alternatively, apertures 120 can comprise an area of first region 114 where a region of the material has been removed or otherwise weakened such that the weakened region at least partially deforms or detaches in response to inflation of expandable member 102 and permits distension beyond the first inflated state. Apertures 120 can be formed by any suitable means, including cutting, stamping, laser cutting, perforating, and/or punching/puncturing and/or the like. In various embodiments, the first region 114 of the cover 104 can comprise a net like structure.

In some embodiments, a therapeutic agent may be disposed on an inner or outer surface of the expandable member 102 or portion of the cover 104, or inside the expandable member 102. For example, a coating comprising a therapeutic agent may be coated on an outer surface 108 of the expandable member 102. As the expandable member 102 protrudes through the apertures 120 the therapeutic agent can be released at a localized portion of the body lumen. The therapeutic agent can comprise a liquid or solid form. Liquid form can be of a desired viscosity suitable for the treatment desired. In some embodiments, the expansion element 101 can also have a coating comprising a therapeutic agent disposed on, inside of, temporarily filling, or otherwise be integrated with one or more of the first region 114, second region 116, and third region 118 of the cover 104.

The expandable member 102 can comprise any suitable compliant expandable member. As described above, a compliant expandable member can comprise a polymeric material. Exemplary materials for a compliant expandable member include elastomers such as polyurethane and silicone, natural rubber or latex products, synthetic rubber such as nitrile butadiene, or other synthetic or naturally occurring polymeric materials. In various embodiments, expandable member 102 may not be fully compliant, but is more compliant than first region 114 of the cover 104 and is sufficiently flexible to inflate to a diameter larger than the diameter of the restraining first region 114 at a given pressure, and thereby produces protrusions 122 of the expandable member 102. Thus, a semi-compliant or non-compliant expandable member can be used. Optionally, the first region 114 of the cover 104 can comprise apertures that vary in size. By increasing the size, the apertures can allow for a wider (or "coarser") protrusion. By combining varying aperture sizes with a tapered cover profile, the "scraping" effect of the assembly can be intensified proximally to distally or vice versa due to the different protrusion heights of the expandable member 102.

In some embodiments of the disclosure, the first region 114 of the cover 104 can comprise a wall having regions of reduced or less compliance than other, more distensible regions of wall. The other regions being essentially the "apertures" that permit the underlying expandable member 102 to expand outwardly relative to the regions of reduced or less compliance of the first region 114 of the cover 104. The more distensible regions can comprise an upper distension limit. The regions of reduced compliance can be formed through laser densification or by imbibing with a polymer that reduces the compliance in the imbibed region. In an embodiment, the regions of reduced compliance have substantially the same thickness as the more distensible regions. Similarly, with other embodiments described herein, the first region 114 of the cover 104 can be formed via tape wrapping or extrusion and can comprise ePTFE or any other material wherein the compliancy can be varied at discrete sites.

In various embodiments of the present disclosure, the first region 114 of the cover 104 can comprise any size-limited form that acts to constrain the expandable member 102 along the points of contact. Alternatively, the first region 114 of the cover 104 can comprise a form less compliant than the expandable member 102 so that the expandable member 102 is constrained along the points of contact. As such, the first region 114 of the cover 104 may be constructed of any material that cannot be appreciably deformed beyond a first inflated state during inflation of the expandable member 102.

With the described components, one can adapt the compliance of at least a portion of the cover and/or adapt an aperture pattern along at least a portion of the cover to control the topography of an expandable member assembly. For example, an aperture pattern can comprise many small apertures to obtain a "fine texture" pattern or can comprise fewer larger openings to obtain a more "coarse texture" pattern. As one can appreciate, any possible aperture pattern, or combinations of aperture patterns, is contemplated herein. For example, a first region of a cover can comprise a square grid like aperture pattern and a second region of the cover can comprise a diamond shaped pattern.

In other embodiments of the present disclosure, an expandable member expanding through a cover can define ridges and troughs which, for example, run parallel to the longitudinal axis of the expandable member. In one embodiment, these provide for blood perfusion between expandable member and vessel wall during a treatment when the expandable member is expanded. In some embodiments, the first region 114 of the cover 104 may not include apertures 120. In some embodiments, the first region 114 of the cover 104 may only include a therapeutic agent coating, for example but not limited to a drug coating.

FIG. 3 depicts the first region 114 of the cover 104 surrounding the expandable member 102 at an inflated profile. As shown in FIG. 4, the expandable member 102 can be deflated and the first region 114 of the cover 104 can be inverted into a cover lumen of the catheter 106 and pulled toward the proximal end 112 of the catheter 106 by an actuator (not shown). As the first region 114 of the cover 104 is pulled through the cover lumen of the catheter 106 the second region 116 of the cover 104 is moved from its position around the catheter 106 and becomes positioned around the expandable member 102. The second region 116 of the cover 104 may have a different surface topography than the first region 114 of the cover 104.

In some embodiments, as depicted in FIG. 4, the second region 116 of the cover 104 may include a plurality of scored portions 124. Upon inflation, as illustrated in FIG. 4, the scored portions 124 will partially separate from a surface 126 of the cover 104 and will form an outwardly extending protrusion. The ruptured portions of cover 104 that is created by the rupture of scores 124 forms apertures 128 in which the expandable member 102 can be at least partially exposed. In various embodiments, one or more of the scores 124 can be formed as a through cut in the material of the second region 116 of the cover which would not have to rupture to achieve the desired effect.

Scoring and later rupturing of scores can enable the insertion of sharp objects into the body in a substantially unsharpened state and then provide for the deployment of the sharp object at a particular time. In addition, scoring and later rupturing can aid in the delivery of therapeutic agents. For example, a therapeutic agent can be disposed between the expandable member 102 and the second region 116 of the cover 104. The cover 104 can seal the therapeutic agent over the expandable member 102 such that when placed into the body, the therapeutic agent is substantially retained in a space between the expandable member 102 and the cover 104. Upon rupture of a scored portion 124 of the cover 104, the therapeutic agent can be released into a localized portion of the body. In some embodiments, the second region 116 of the cover can remove plaque and/or other deposits from a wall of the lumen. In some embodiments, a therapeutic coating may have been applied to the wall of the lumen by the first region 114 prior to removing the plaque and/or other deposits from the wall with the scored portions 124 of the second region 116 of the cover 104, without having removed the medical device 1100 from the lumen.

Any of a variety of additional or alternative expansion element features are contemplated, including scoring and cutting features and the like, drug coatings, controlled topography features, and/or off axis expansion features, for example, among others. Additionally, the expansion element may take any of a variety of forms, including cages, meshes, stents, oscillating members and the like.

Examples Using Diametrically Varied Expansion Elements

In order to achieve graduating expansion diameters, in some examples, a plurality of expansion elements (e.g., balloons) of varying nominal sizes (e.g., diameters) are employed as part of the treatment program. In particular, a graduating set of nominal diameter expansion elements may be employed one, after the other in order to vary the maximum diametric expansion to which tissue is exposed. In some examples, the medical device 1100 may include a plurality of balloon catheters that may be coupled to the pressure modulator 1104, each of the balloon catheters including balloons of varied diameters. In still further examples, a single catheter includes multiple expansion elements having different nominal values.

Examples Using Diametrically Adjustable Expansion Elements

In order to achieve graduating expansion sizes (e.g., diameters), some examples include use of an expansion element incorporating multiple nominal sizes, or stop points, that are exhibited or otherwise achieved under different expansion forces (e.g., pressures). It should be understood that this practice may be used in combination with or as an alternative to use of multiple, expansion elements of different nominal sizes (described above).

Various diametric expansion features (nominal size limits and characteristics) may be implemented to achieve varying (e.g., graduating) nominal sizes. One or more of the base layers forming the balloon or a cover of the balloon can be designed to have a stop point or stop points in a radial and/or axial direction. For example, U.S. Pat. App. Pub. 2014/0172066 filed Dec. 18, 2013 describes balloon devices that utilize an expanded polymer such as a fluoropolymer material that is optionally imbibed with an elastomer.

Upon inflation, the balloon is circumferentially distensible up to a stop point beyond which the force required to distend is markedly increased. The stop point may be a result of material incorporating stored length features. This "stored length" feature may be incorporated into the base material of the balloon or a cover of the balloon. In some examples, a serpentine-shaped fibril microstructure of the fluoropolymer material accounts for at least a portion of the stored length feature and radial distention capability. In addition, such balloon devices can be also appropriately longitudinally distensible (or longitudinally weak) thereby giving or increasing in longitudinal length under the longitudinal stress that may otherwise occur during radial expansion.

In some methods of making such balloons, construction proceeds by circumferentially wrapping (either to form a base layer, or a cover layer of the balloon) elastomer-imbibed expanded polymeric material having stored length at a delivery diameter. Regardless, in various examples such balloons may be expanded up to a first limit, or stop point at a first pressure and then expanded beyond the first limit to a second limit, or stop point at a second, higher pressure. In this manner a nominal size of the balloon (e.g., diameter and/or length) may be adjusted in a stepwise fashion. By incorporating additional stored length layer(s) at different diameter(s), multiple stop points may be achieved for any of the expansion elements described herein as desired.

A variety of additional and/or alternative expansion element constructions and expansion features. For example, additional balloon designs such as any of those disclosed in U.S. Pat. No. 5,752,934 filed Sep. 18, 1995 and Applicant's provisional patent application, U.S. 62/661,942, filed Apr. 24, 2018 may be implemented for the expansion element design as desired.

Pressurizing Source Examples

The pressurizing source 1104 may be coupled to the catheter 15 via a port 26 of the catheter 15. The pressurizing source 1104 may be any suitable inflation-deflation device, such as a syringe, an endoflator/insufflator/inflator, pump or any other apparatus for conducting inflation fluid through the catheter 15 and into the expandable member 20. Additional examples can include one or more of a piston drive, a screw drive, an air compressor, a gas cartridge, a servo motor, a piezo electric motor, and/or a pressurized fluid reservoir, for example, among others. The pressurizing source 1104 may include a manual component (e.g., a syringe stopper) coupled to an automated component (e.g., an air cylinder, air compressor, or other suitable component).

In accordance with some embodiments, the pressurizing source 104 pushes fluid into and retracts fluid from the chamber of the expandable member (e.g., expandable member 20) via the catheter to inflate and deflate the expandable member. The pressurizing source 1104 may include a fluid reservoir (not shown) or be connected to a separate fluid reservoir (also not shown). To assist in the control of the diameter of the expandable member(s), the catheter of the medical device 1100 may be aspirated (remove air and replace it with a fluid) prior to inflating the expandable member with inflation fluid. The inflation fluid used to aspirate the catheter and the expandable member and/or to inflate the expandable member may comprise a contrast (e.g., an imaging agent that allows the expandable member to be imaged by an imaging modality), or a mixture of a contrast and saline.

Controller Examples

The controller 1106 optionally includes one or more mechanical timing mechanisms, such as gears, linkages, or other mechanisms for causing the medical device to cycle in size according to the predetermined treatment program. In some examples, the treatment program 1110 and its various features and components can be implemented in one or more computing devices (e.g., personal computer, laptop, server, controller) that contain one or more processors and memory. For example, the treatment program 1110 may be implemented using firmware, integrated circuits, and/or software modules within the one or more computing devices that interact with each other or are combined together. In certain embodiments, the methods disclosed herein for the treatment program 1110 and outlined in the figures can be implemented using computer-readable instructions/code that are stored in memory (or other forms of storage) for execution by the one or more processors.

In some embodiments, the memory includes computer-readable media in the form of volatile and/or nonvolatile memory and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; and/or any other medium that can be used to store information and can be accessed by a computing device such as, for example, quantum state memory, and/or the like. In some embodiments, the memory stores computer-executable instructions for causing the processor of the controller 1106 to implement aspects of embodiments of system components discussed herein and/or to perform aspects of embodiments of methods and procedures discussed herein.

The computer-executable instructions may include, for example, computer code, machine-useable instructions, and the like such as, for example, program components capable of being executed by one or more processors associated with the controller 1106. Program components may be programmed using any number of different programming environments, including various languages, development kits, frameworks, and/or the like. Some or all of the functionality contemplated herein may also, or alternatively, be implemented in hardware and/or firmware.

The controller 1106 may be configured to operate the medical device 1100 according to the treatment program 1110 or portions thereof and may be a separate component or included in any of the other system components, such as the pressurizing source 1104, power source 1108 or medical device 1100 as desired. The controller 1106 may be include or be connected to a separate user interface (not shown). The controller 1106 can include at least one processor (e.g., microprocessor) that executes software and/or firmware stored in memory of the controller 1106. The software/firmware code contains instructions that, when executed by the processor, cause the controller 1106 to operate the medical device 1100 according to the treatment program 1110. The controller 1106 may alternatively include one or more application-specific integrated circuits (ASICs), field-programmable gate arrays (FPGAs), digital signal processors (DSPs), hardwired logic, or combinations thereof.

In some examples, the controller 1106 receives information from a plurality of system components (e.g., pressure sensors, current sensors, feedback loops, or other information sources of any of the components) and feeds the information (e.g., pressure data, drug delivery data, user data) into a control algorithm which determines at least one treatment program parameter which may in part govern operation of the medical device 1100. In some specific embodiments, the controller 1106 may receive expansion element data from the medical device 1100 and/or pressurizing source 1102 (e.g., balloon pressure, whether measured directly or indirectly by a proxy such as current change in an electric motor) and user data from the user interface (not shown). In certain embodiments, the controller 1106 receives user data from a device located remotely (e.g., a server, a physician's computing/communication device, and the like).

Power Source Examples

In both automated and non-automated examples, the power source 1108 may include a physical user input, such as turning a handle (e.g., where a mechanical timing mechanism is used to achieve the treatment program). The power source may also be electrical, chemical, or electro-chemical in nature. In some examples, the power source 1108 is a battery housed with other components of the system 1102.

Test System

Figure 5A:
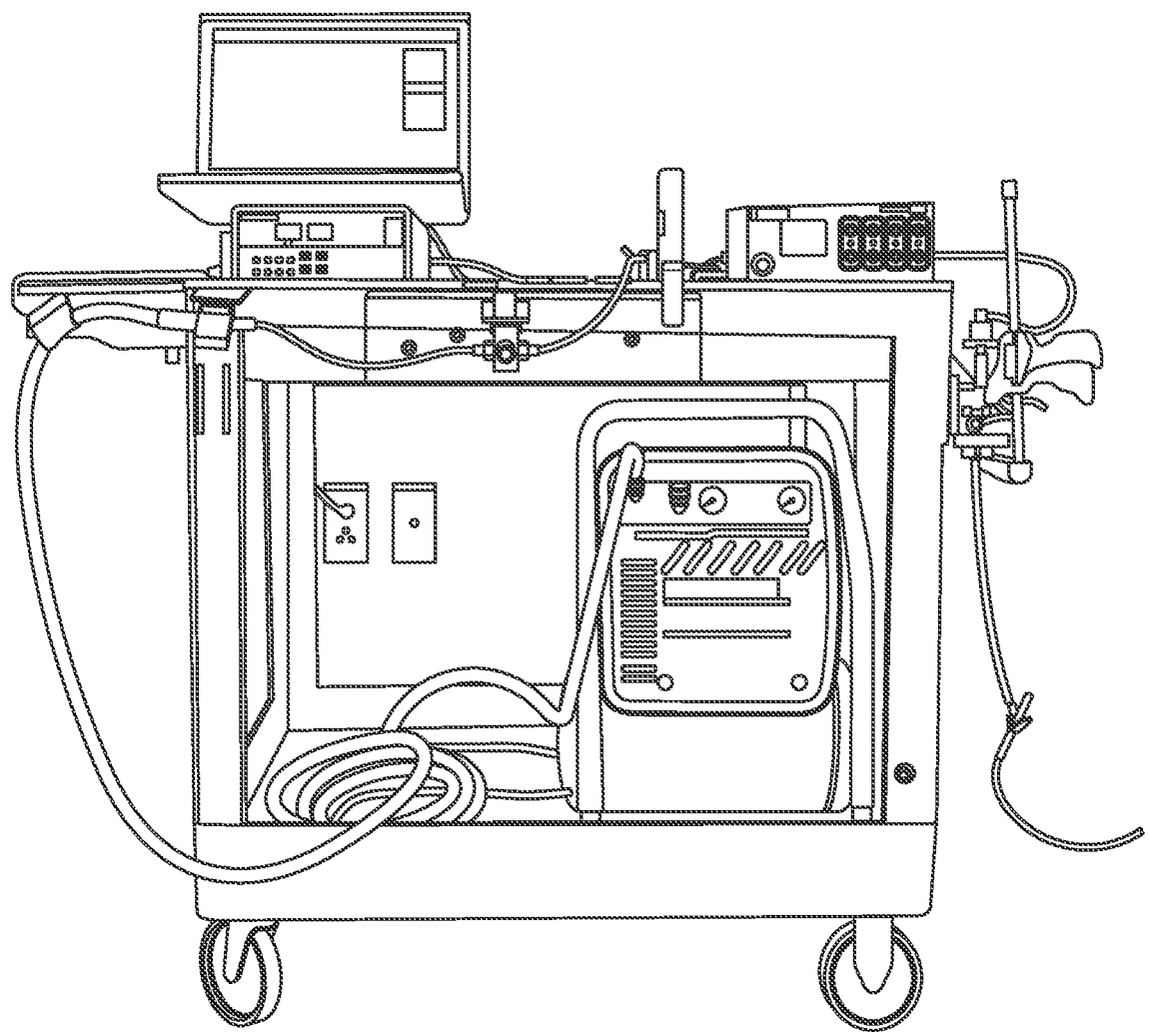
FIGS. 5A to 5C illustrate a test apparatus according to the system of FIG. 1, according to some examples.
Figure 5B:
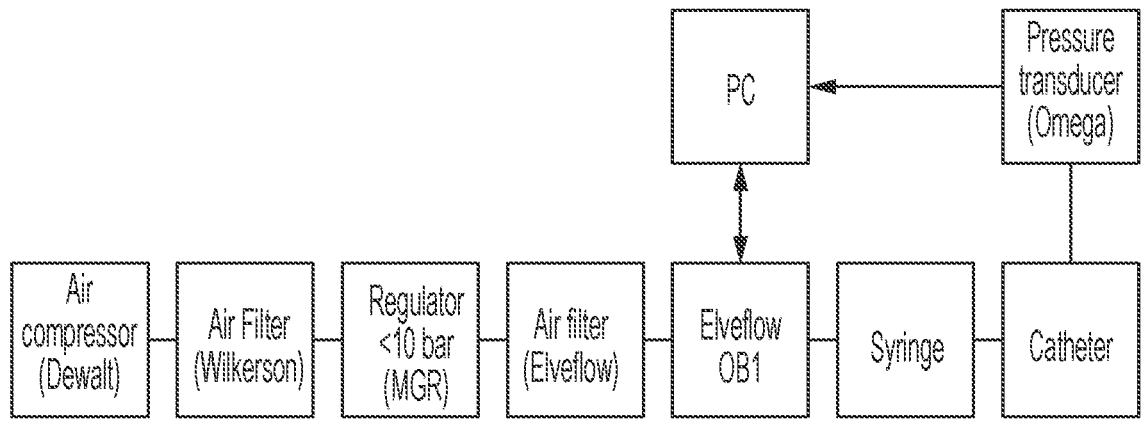
Figure 5C:
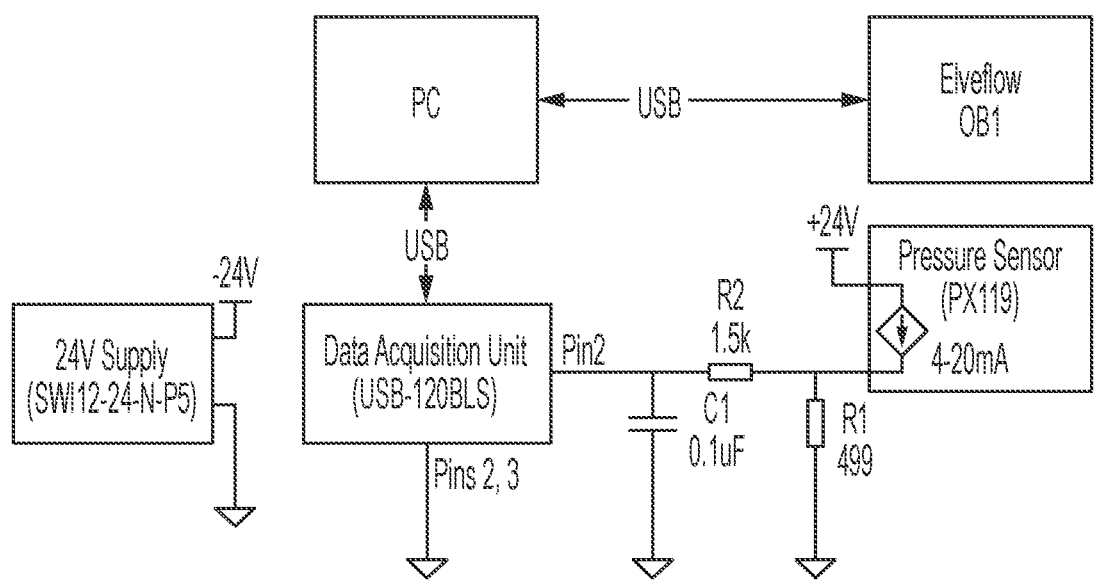

FIGS. 5A and 5B illustrates a test apparatus for assessing treatment program efficacy, according to various examples. As shown in FIG. 5A, in the test apparatus, the pressurizing source 1104 (FIG. 1) includes a microfluidic flow control system including one or more pressure and/or vacuum pumps, such as those sold under the trade name "Elveflow," a flow regulator, air filter, and air compressor, and a syringe for pressurizing a catheter serving as the medical device 1100 (FIG. 1). The controller 1106 (FIG. 1) includes a laptop PC and the power source 1108 includes an electrical outlet. FIG. 5B is a schematic representation of various system components for further understanding. FIG. 5C is a block diagram of one design for the controller for controlling the pressurizing source, according to some examples. In some embodiments, the pressure sensor is a 4-20 mA transmitter that pulls 4 mA when it is measuring 0% and 20 mA when 100%. A 499-ohm resistor may be used to convert current to a voltage and an RC filter may be used to reject switching noise from the 24V power supply. Data from the system may be logged to verify treatment program efficacy and/or to provide a closed feedback loop to the system as desired.

Treatment Program Parameters

As previously indicated, the treatment program or portions thereof may be carried out manually or may be automated through use of mechanical or electronic methods.

In some examples, the treatment program includes cycling the expansion element between enlarged and contracted states, or configurations at a desired frequency (including any range of frequencies). In some examples, the treatment program includes cycling the expansion element at a first frequency (e.g., from 0.1 to 10 Hz), at a second frequency different from the first frequency (e.g., from 0.1 to 10 Hz), at a third frequency different from the first and/or second frequencies, and so forth. In addition to changes in frequency, the treatment program may vary in minimum expansion size/pressure per cycle, maximum expansion size/pressure per cycle, cycle amplitude, cycle frequency, dwell time, and total program length, for example, among others. Additionally, the treatment program may be configured to treat a particular tissue site and/or type of medical treatment, for example.

The following table lists non-limiting examples of expected pressure ranges, balloon types used for the medical device 1100, pressure increments, cycle frequency, a calcium score for a particular tissue site to which the treatment program would be applied, nominal balloon diameters that may be used for the medical device 1100, and disease types for which the treatment program would be configured/applied. These various parameters may be combined in any desired combination, and each of the ranges include not only the specific ranges called out in the table below, but any value or range in between the values called out in the Table 1 below. In other words, Table 1 should not be read as limiting in nature, but instead of inventive concepts within the scope of this disclosure.

expanded and contracted between a first size $D1n$ at a corresponding first force $F1n$ and a second size $D2n$ at a corresponding force $F2n$ that is greater than the first size $D1n$ and the first force $F1n$, respectively. The first and/or second sizes and forces can graduate, remain constant, or decrease throughout the treatment program 1110 as desired.

Figure 6:
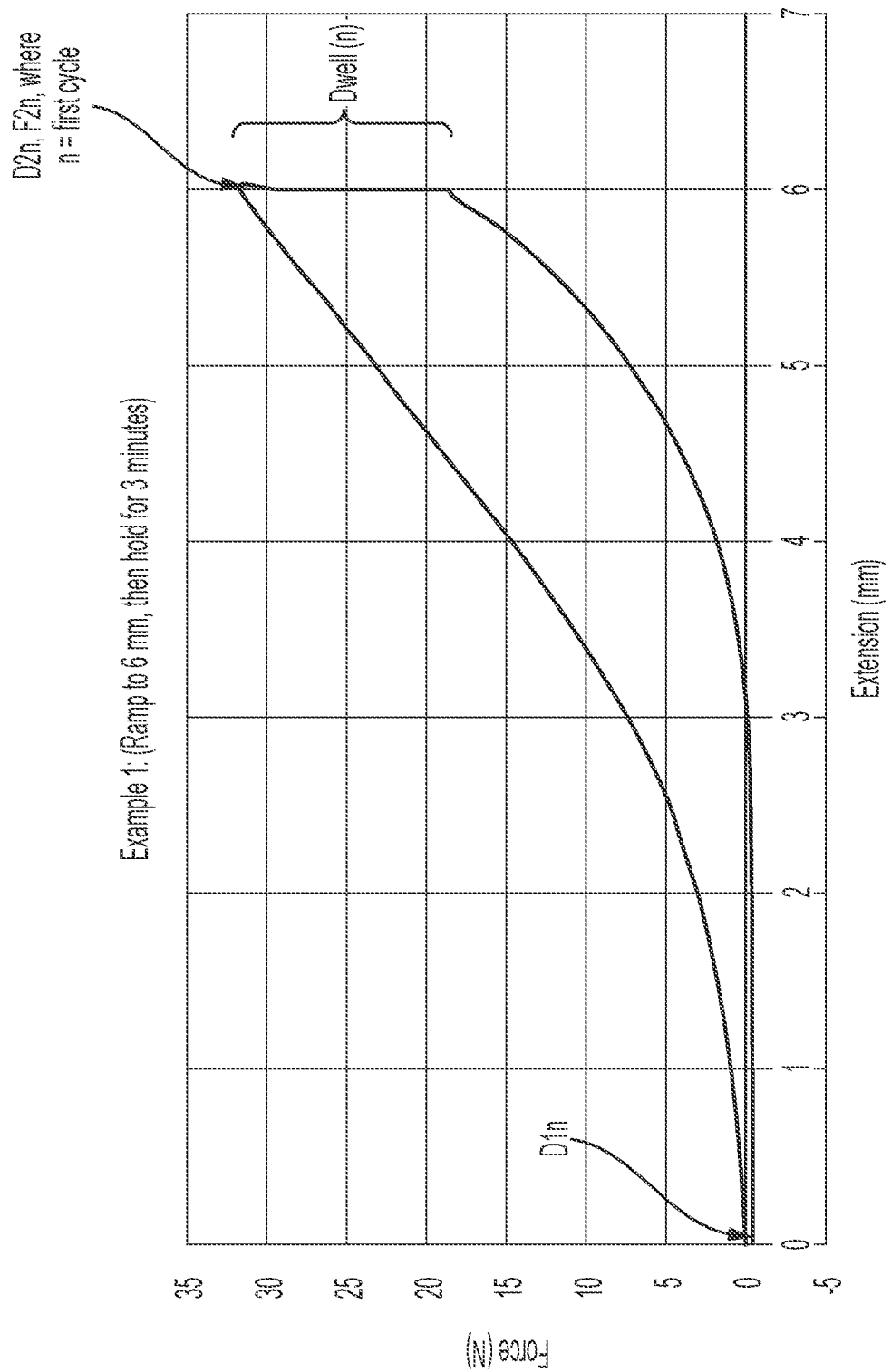
FIGS. 6 to 11 illustrate various treatment programs or portions thereof, according to some examples.

FIG. 6 is an example of a treatment program (or portion thereof) in which one or more expansion elements are expanded and contracted at a treatment frequency having a value from 0.1 Hz to 10 Hz, the one or more expansion elements being expanded and contracted between a first size $D1n$ and a second size $D2n$ that is greater than the first size $D1n$. In the example shown in FIG. 6, a single cycle is shown (n=1) and the treatment profile includes a hold time, or dwell time Dwell(n), at the second size for three minutes (min), although any of a variety of dwell times ranging from 1 second (s) to 60 minutes (min), including any value or any range of values therebetween in 1 second (s) intervals. In the Example 1 of FIG. 6, the maximum force imparted by the associated expansion element ranges from 0 Newtons (N) to over 30 Newtons (N), although any of a variety of forces, including any value or any range of values therebetween in 0.5 Newton (N) intervals of total force N are contemplated. After the dwell time Dwell(n), the expansion element is allowed to contract and return to an extension of about 0 millimeters (mm), for example.

Figure 7:
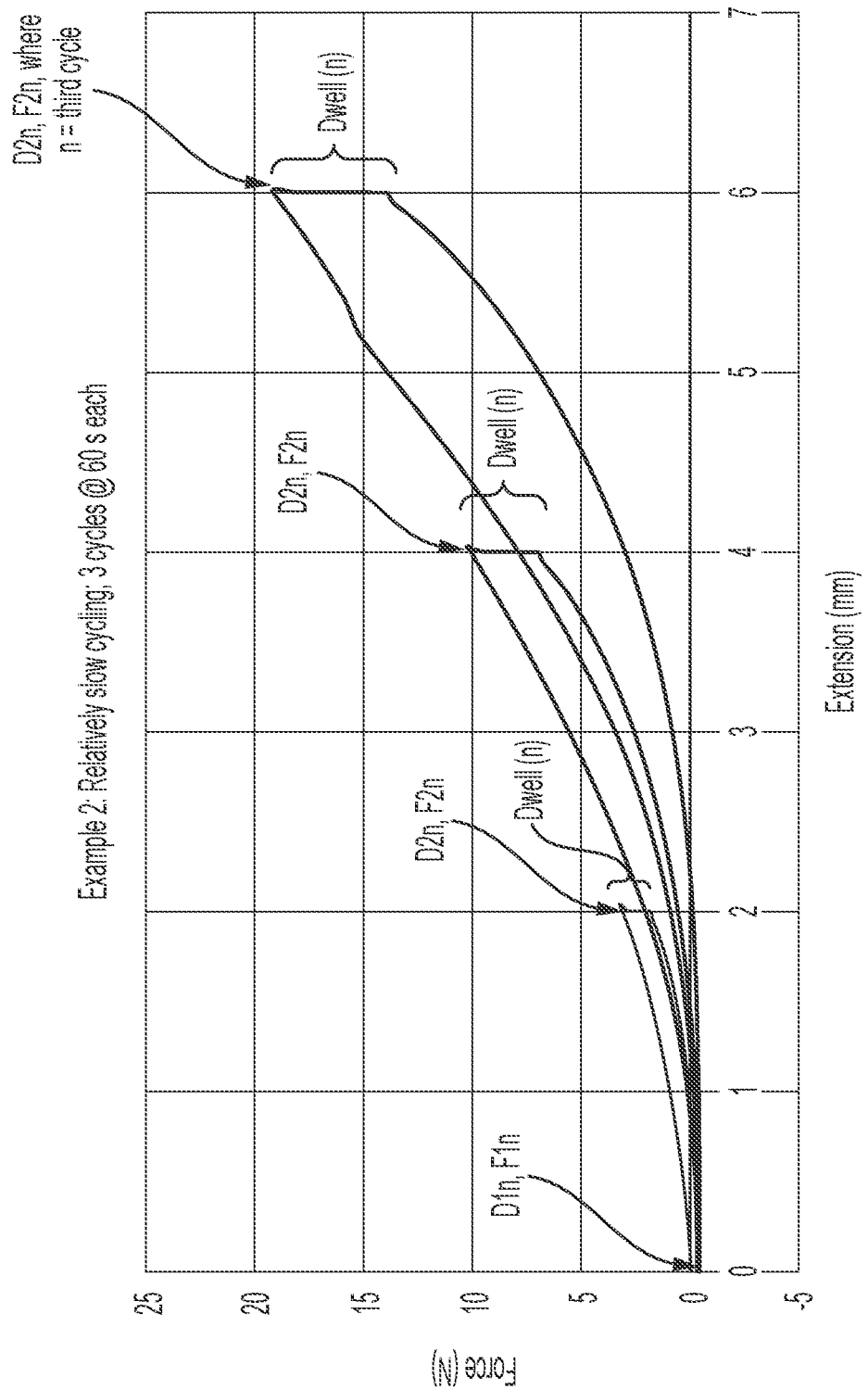

FIG. 7 is an example of a treatment program (or portion thereof) in which one or more expansion elements are expanded and contracted at a treatment frequency having a value from 0.1 Hz to 10 Hz, the one or more expansion elements being expanded and contracted between a first size $D1n$ and a second size $D2n$ that is greater than the first size $D1n$ through a graduating, cyclic expansion profile including the second size $D2n$ graduating in value from an initial

TABLE 1

| Parameter | Range 1 | Range 2 | Range 3 |
| --- | --- | --- | --- |
| Pressure (atm) | 0-20 | 1-12 | 1-6, 3-9, 3-10, 3-15 |
| Balloon | 0-Rated burst pressure | 1-Nominal inflation pressure | |
| Vessels | All | Peripheral | |
| Pressure Increments (atm) | 0.01-5 atm | 0.25-2 | 0.01-2, 0.02-3, 0.1-2, 0.2-3, 0.3-4, 0.2-4, 0.25-2.5, 0.2-2.5, 0.5-3, 0.5-4, 1-3, 1-4, 1-5, 1-6, 2-3, 2-4, 2-5, 2-6, 2-7, 2-10, 2-NIP, 2-RBP, 1-NIP, 1-RBP |
| Frequency (Hz) | 0.01-20 | 0.1-5 | 0.05-2, 0.05-3, 0.06-4, 0.2-5, 0.25-3, 0.3-3, 0.3-5, 0.4-2, 0.4-3, 0.4-10, 1-11, 1-12, 0.1-12, 1-15, 5-10, 10-15 |
| Calcium Score | 0-extreme | mild to moderate | Luminal, medical intimal, Mockenberg, circumferential |
| Diameters (mm) | 0-40 | 2-14 | 1-15, 3-13, 4-12, 5-11, 6-10, 2-12, 5-10, 10-15 10-20, 10-25, 10-30 5-15, 5-20, 5-30, 10-30 10-35, 20-35 |
| Disease | PAD AV Access Venous Kyphoplasty Sinuplasty Skin expansion | PAD AV Access Venous | |

Treatment Program Cyclic Expansion/Treatment Profiles

Each of the following examples relates to a treatment profile for a treatment program (or portion thereof) in which one or more expansion elements are expanded and contracted at a treatment frequency having a value from 0.1 Hz to 10 Hz, the one or more expansion elements being value $D2n$ that is greater than the nominal size of a treatment site and a subsequent value $D2n+1$ that is greater than the initial value $D2n$ to which the expansion element is expanded, where n ranges from 0 to the total number of cycles (3 cycles in Example 2 of FIG. 7, although any number is contemplated). As shown, the second value graduates in extension by at about 2 mm increments with concomitant graduating force values, although any of a variety of incremental graduations are contemplated.

For each cycle in Example 2 of FIG. 7, the treatment profile includes a hold time, or dwell time Dwell(n), at the second size for 60 seconds (s), although any of a variety of dwell times ranging from 1 second (s) to 60 minutes (min), including any value or any range of values therebetween in 1 second (s) intervals. After each cycle's dwell time Dwell (n), the expansion element is allowed to contract and return to an extension of about 0, for example, although in other examples another cycle begins prior to the extension returning toward (e.g., approaching, or moving in a direction of) zero.

Figure 8:
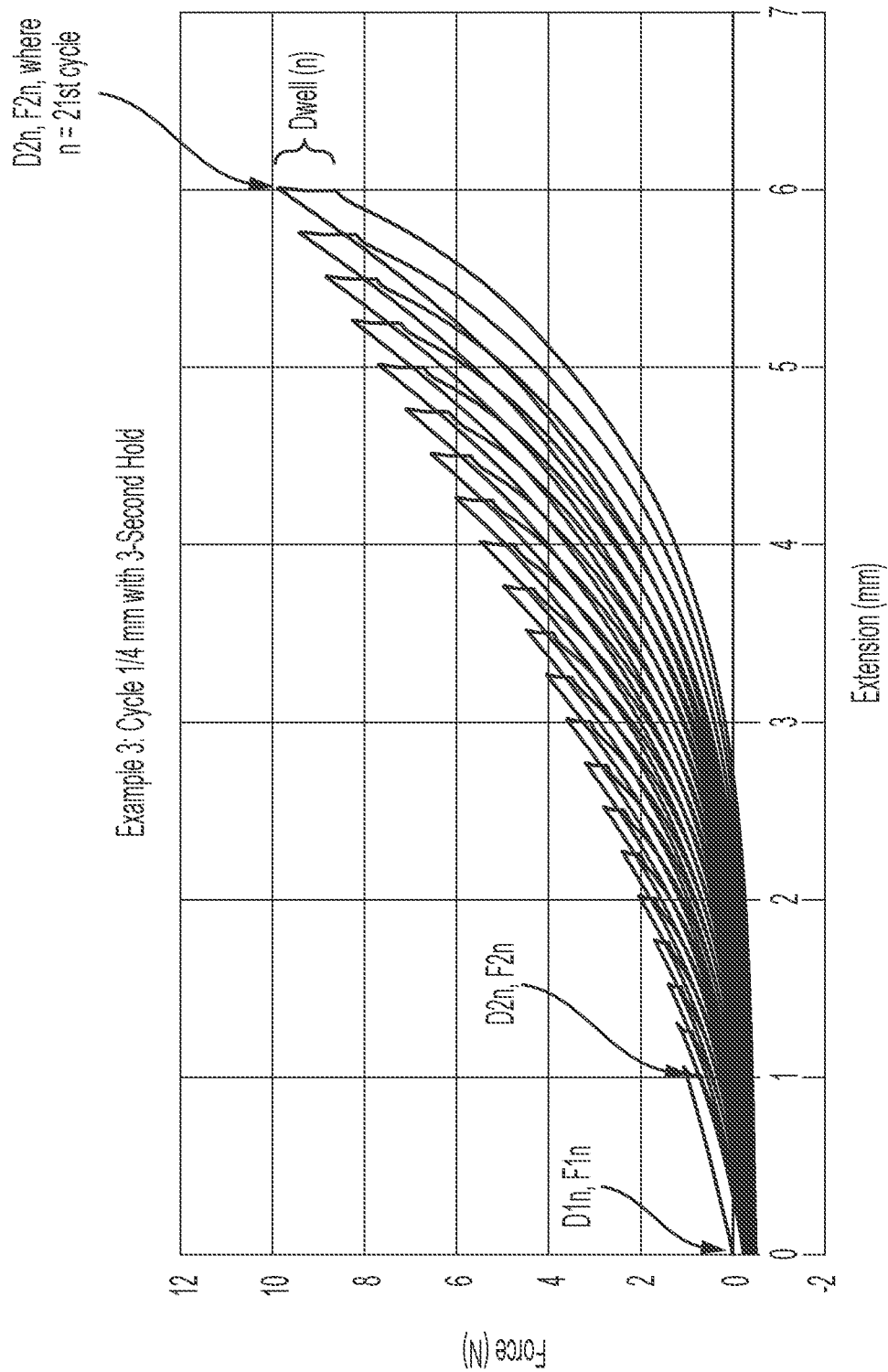

FIG. 8 is another example of a treatment program (or portion thereof) in which one or more expansion elements are expanded and contracted at a treatment frequency having a value from 0.1 Hz to 10 Hz, the one or more expansion elements being expanded and contracted between a first size $D1n$ and a second size $D2n$ that is greater than the first size $D1n$ through a graduating, cyclic expansion profile including the second size $D2n$ graduating in value from an initial value $D2n$ that is greater than the nominal size of a treatment site and a subsequent value $D2n+1$ that is greater than the initial value $D2n$ to which the expansion element is expanded, where n ranges from 0 to the total number of cycles.

As shown in FIG. 8, the second value graduates in extension/size by about 0.25 mm increments with concomitant graduating force values, although any of a variety of incremental graduations are contemplated.

For each cycle in Example 3 of FIG. 8, the treatment profile includes a hold time, or dwell time Dwell(n), at the second size for 60 seconds (s), with an increasing amount of force relaxation exhibited during the dwell time Dwell(n) for each cycle. Any of a variety of dwell times ranging from 0 seconds (s) to 1 second (s) to 60 minutes (min), including any value or any range of values therebetween in 1 second (s) intervals, for example, is contemplated. After each cycle's dwell time Dwell(n), the expansion element is allowed to contract and return to an extension of about 0, for example, although in other examples another cycle begins prior to the extension returning toward (e.g., approaching, or moving in a direction of) zero.

Figure 9:
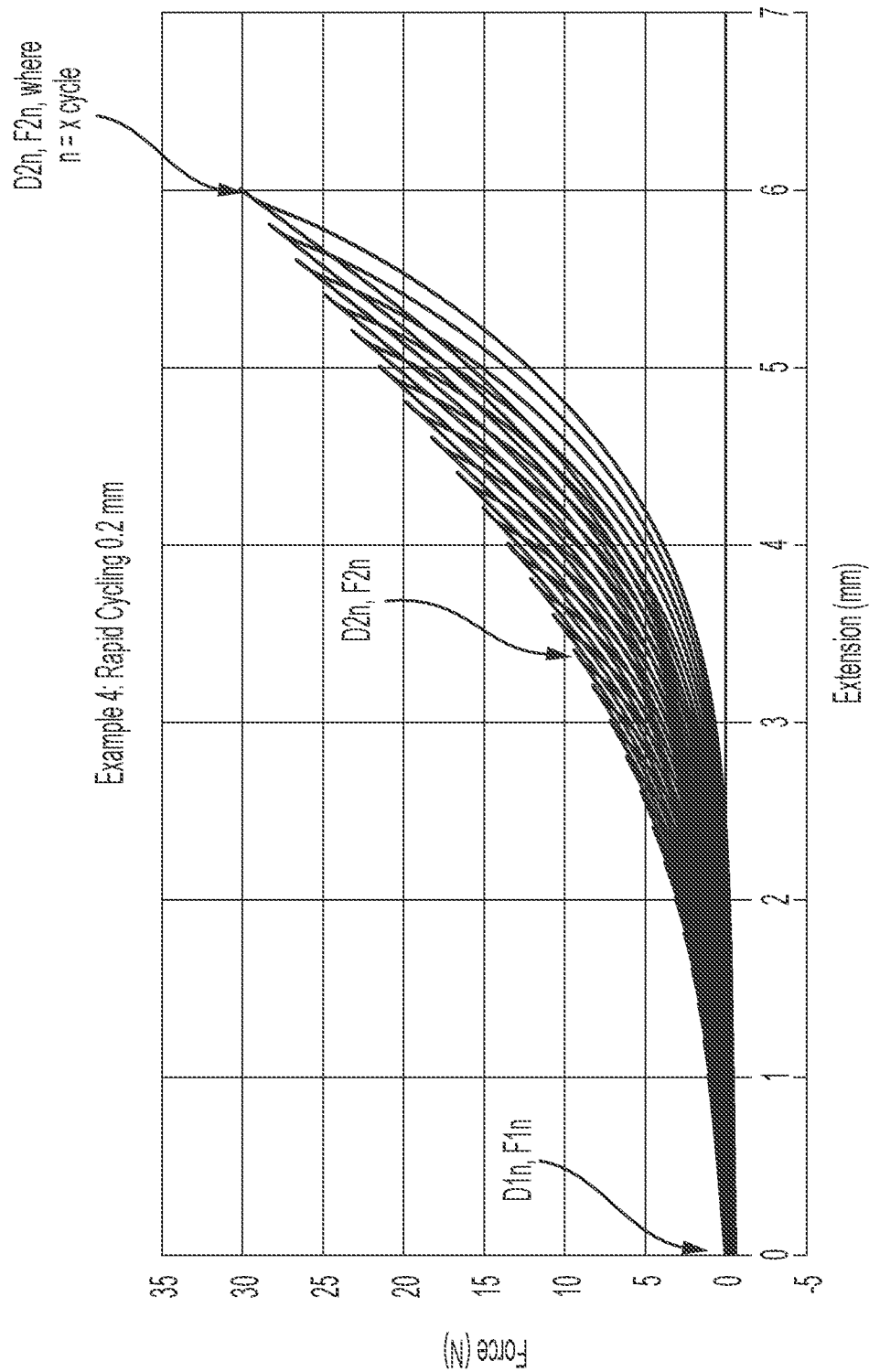

FIG. 9 is still another example of a treatment program (or portion thereof) in which one or more expansion elements are expanded and contracted at a treatment frequency having a value from 0.1 Hz to 10 Hz, the one or more expansion elements being expanded and contracted between a first size $D1n$ and a second size $D2n$ that is greater than the first size $D1n$ through a graduating, cyclic expansion profile including the second size $D2n$ graduating in value from an initial value $D2n$ that is greater than the nominal size of a treatment site and a subsequent value $D2n+1$ that is greater than the initial value $D2n$ to which the expansion element is expanded, where n ranges from 0 to the total number of cycles.

As shown in FIG. 9, the second value graduates in extension/size by about 0.2 mm increments with concomitant graduating force values, although any of a variety of incremental graduations are contemplated.

For each cycle in Example 4 of FIG. 9, the treatment profile includes no hold time, or dwell time Dwell(n) of zero at the second size $D2n$ for each cycle. After each cycle's, the expansion element is immediately, or nearly immediately allowed to contract and return to an extension of about 0, for example, although in other examples another cycle begins prior to the extension returning toward (e.g., approaching, or moving in a direction of) zero.

Figure 10:
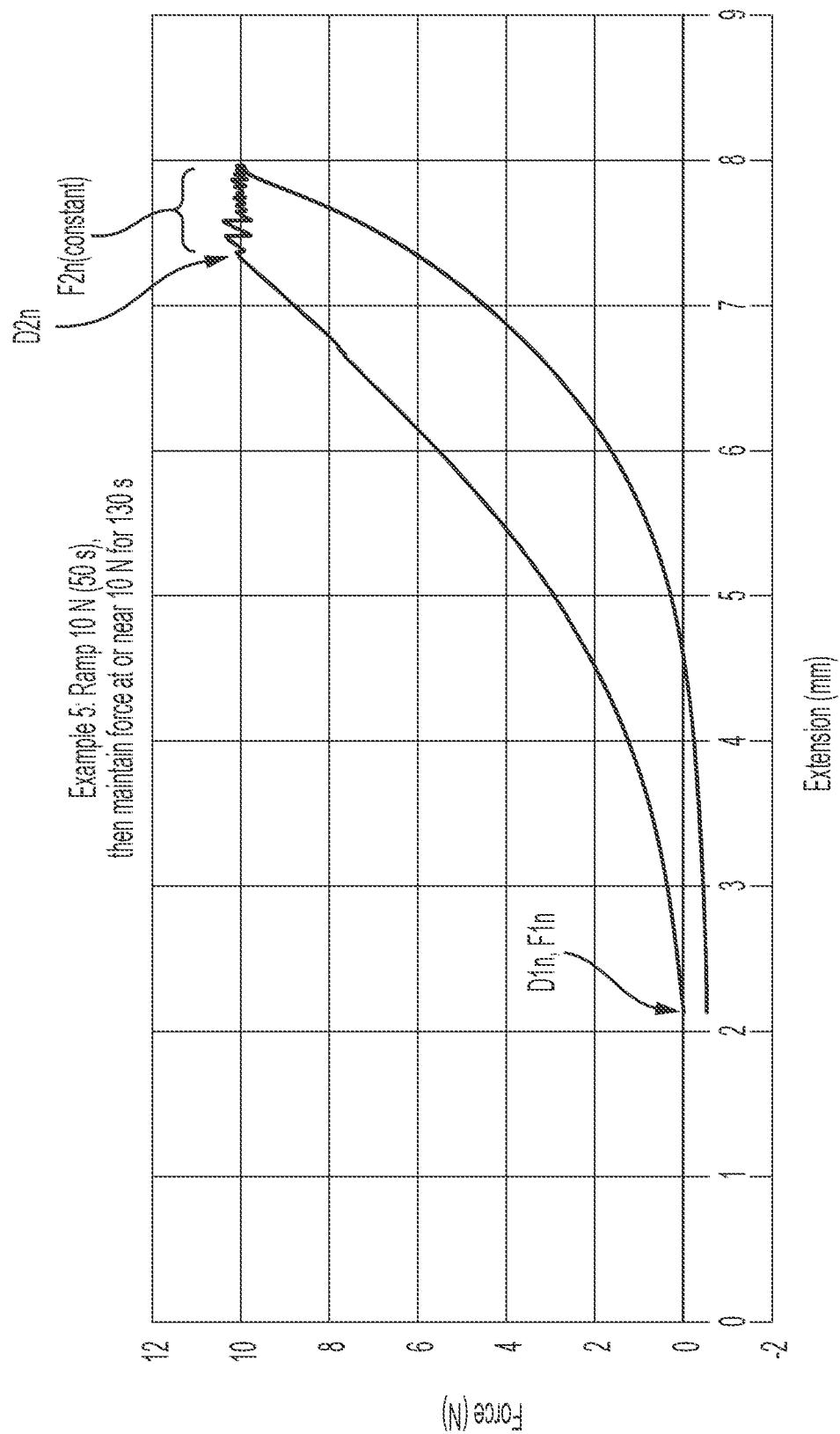

FIG. 10 is still another example of a treatment program (or portion thereof) in which one or more expansion elements are expanded and contracted at a treatment frequency having a value from 0.1 Hz to 10 Hz, the one or more expansion elements being expanded and contracted between a first size $D1n$ and a second size $D2n$ that is greater than the first size $D1n$. A single cycle is shown, although multiple cycles may be employed.

As shown in FIG. 10, the second force $F2n$ is maintained relatively constant (e.g., through use of a closed feedback loop measuring inflation pressure on the expansion element) for a desired period (e.g., 130 seconds (s), although any force maintenance period is contemplated). During the constant force period $F2n$(constant) the extension, or size increases by a desired amount (e.g., 0.7 millimeters (mm), although any value is contemplated).

Figure 11:
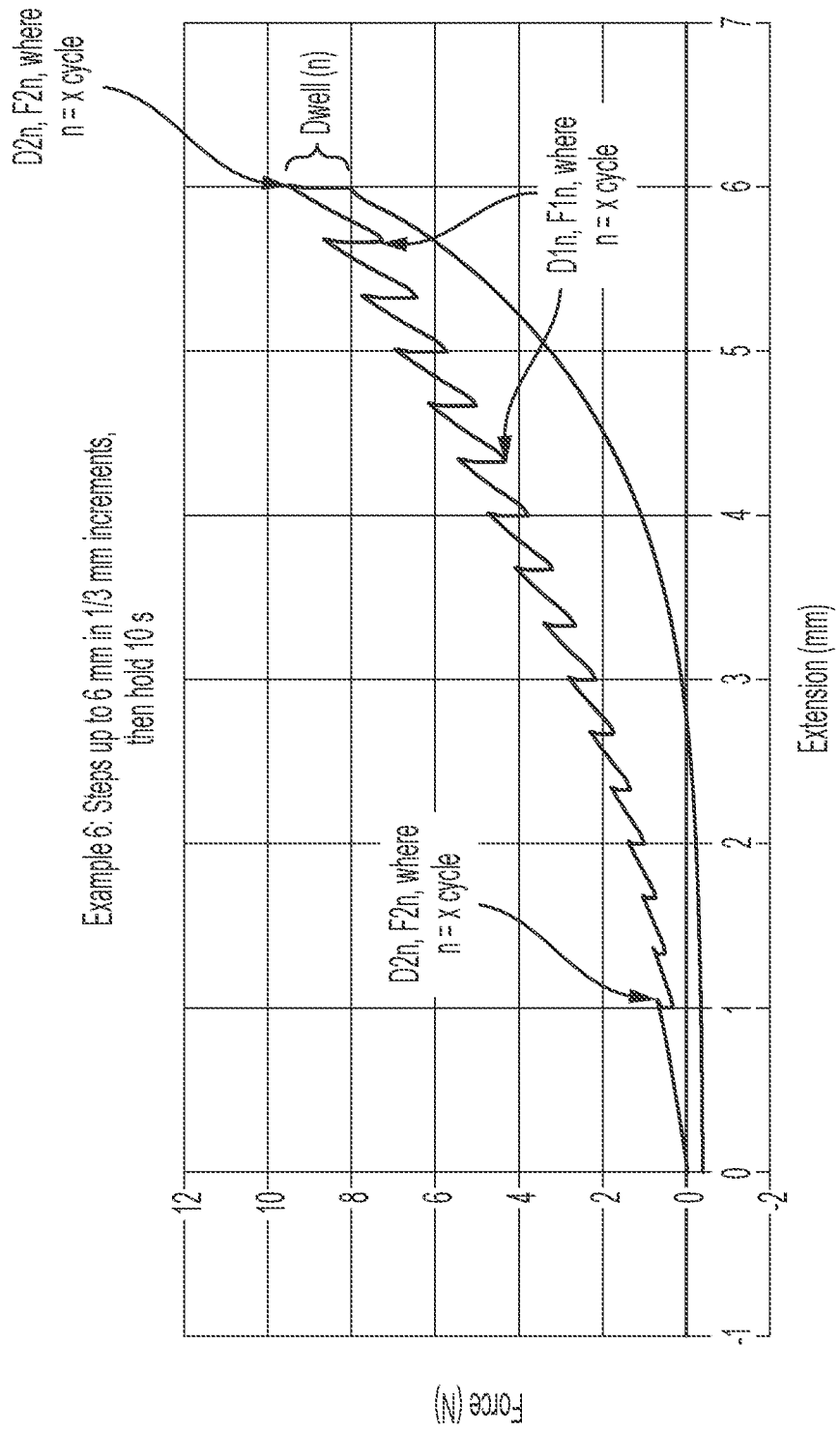

FIG. 11 shows another example of a treatment program or portion thereof, Example 6, in which one or more expansion elements are expanded and contracted at a treatment frequency having a value from 0.1 Hz to 10 Hz, the one or more expansion elements being expanded and contracted between a first size $D1n$ and a second size $D2n$ that is greater than the first size $D1n$ through a graduating, cyclic expansion profile including the second size $D2n$ graduating in value from an initial value $D2n$ that is greater than the nominal size of a treatment site and a subsequent value $D2n+1$ that is greater than the initial value $D2n$ to which the expansion element is expanded, where n ranges from 0 to the total number of cycles. Moreover, the first size $D1n$ also graduates in value from an initial value $D1n$ and a subsequent value $D1n+1$ that is greater than the initial value $D1n$, where n ranges from 0 to the total number of cycles.

As shown in FIG. 1, the second value $D2n$ graduates in extension/size by about 0.3 mm increments with concomitant graduating force values (increasing cycle-to-cycle), although any of a variety of incremental graduations are contemplated. Similarly, the first value $D1n$ graduates in extension/size with concomitant graduating force values (increasing cycle-to-cycle), although any of a variety of incremental graduations are contemplated.

For each cycle in Example 6 of FIG. 11, the treatment profile includes a dwell time Dwell(n) for each cycle, with an increasing force relaxation exhibited at during the dwell time Dwell(n) for each cycle. After each cycle, the expansion element is immediately, or nearly immediately allowed to contract and return to an extension of about 0, for example, although in other examples another cycle begins prior to the extension returning toward (e.g., approaching, or moving in a direction of) zero.

Any of the foregoing treatment profile characteristics may be combined, modified, or augmented with those of other treatment profiles.

In any example, the second size $D2n$ may be constant for each cycle, graduate for each cycle, or graduate and/or decrease for alternating cycles. The second size $D2n$ may graduate at a constant rate or a varying rate. The second size $D2n$ may graduate as a percentage of the prior second size value $D2n$ by 10% to 500%, including any value in that range or any range within that range in 0% increments.

In any example, the first size $D1n$ may be constant for each cycle, graduate for each cycle, or graduate and/or decrease for alternating cycles. The first size $D1n$ may graduate at a constant rate or a varying rate. The first size $D1n$ may graduate as a percentage of the prior first size value D1$n$ by 0% to 500%, including any value in that range or any range within that range in 1% increments.

In any example, the dwell time Dwell(n) may be constant for each cycle, graduate for each cycle, or graduate and/or decrease for alternating cycles. The dwell time Dwell(n) of the cycles may change at a constant rate or a varying rate. The dwell time Dwell(n) may change as a percentage of the prior dwell time Dwell(n) by 0% to 500%, including any value in that range or any range within that range in 1% increments.

Similarly, in any example, the treatment program may exhibit a relatively constant amount of force relaxation during each dwell time Dwell(n), an increasing amount of force relaxation during subsequent dwell times Dwell(n), or variable force relaxation relative to a prior dwell time Dwell(n) depending upon a particular cycle of the treatment program.

The amplitude change for each cycle, or the difference between D1$n$ and D2$n$ may be constant for each cycle, graduate for each cycle, or graduate and/or decrease for alternating cycles. The amplitude may change at a constant rate or a varying rate. The amplitude per cycle may change as a percentage of the prior cycle amplitude by 0% to 500%, including any value in that range or any range within that range in 1% increments.

Moreover, rather than size, the treatment program may be expressed in terms of force (e.g., stress or pressure). In any example, the second force F2$n$ may be constant for each cycle, graduate for each cycle, or graduate and/or decrease for alternating cycles. The second force F2$n$ may graduate at a constant rate or a varying rate. The second force F2$n$ may graduate as a percentage of the prior second force value F2$n$ by 10% to 500%, including any value in that range or any range within that range in 0% increments.

In any example, the first force F1$n$ may be constant for each cycle, graduate for each cycle, or graduate and/or decrease for alternating cycles. The first force F1$n$ may graduate at a constant rate or a varying rate. The first force F1$n$ may graduate as a percentage of the prior first force value F1$n$ by 0% to 500%, including any value in that range or any range within that range in 1% increments.

In any example, the treatment program may include providing a cycle in which the first size D1$n$ and a second size D2$n$ represent a first diameter and a final diameter. The final diameter is the largest diameter and represents the desired final diameter in the treatment protocol for that cycle. However, the treatment program may include any number of intermediate diameters Dintn which is larger than D1$n$ and smaller than D2$n$. The treatment protocol may include beginning at the first size D1$n$ and inflating to the second or final diameter D2, with preference for cycling between the first diameter D1$n$ and the intermediate diameters Dintn, up to the second or final diameter D2$n$, wherein cycling between the first diameter D1$n$ and the intermediate diameters Dintn include progressively increasing the intermediate diameter Dintn until the second diameter D2$n$ is achieved. A specific example might include cycling from the first diameter D1$n$ to a first intermediate diameter Dint1, back to the first diameter D1$n$, up to a second, larger intermediate diameter Dint2, back to the first diameter D1$n$, and up to a third, even larger intermediate diameter Dint3, until the cycle reaches the target, second or final diameter D2$n$.

In other embodiments, the cycling may include cycling from the first diameter D1$n$ to a first intermediate diameter Dint1, back to the first diameter D1$n$, up to a second, larger intermediate diameter Dint2, back to the first intermediate diameter Dint1, up to a third, even larger intermediate diameter Dint3, and back to second intermediate diameter Dint2 the until the cycle reaches the target, second or final diameter D2$n$. It is within the scope of the disclosure that a combination of the various cycling protocols may include a combination of the above disclosed cycles, wherein the diameter may be incrementally increased after each drop in pressure either to the first diameter D1$n$ or to a previous intermediate diameter Dintn (either the immediately preceding intermediate diameter Dintn or any intermediate diameter Dintn preceding the current intermediate diameter Dintn).

Thus, in some configurations, the target site or the vessel to be treated has a starting vessel diameter and a target finished vessel diameter, wherein the starting vessel diameter is smaller than the target finished vessel diameter. The second diameter D2$n$ of the expansion element is configured to achieve the target finished vessel diameter. In some embodiments, the expansion element includes a stop that limits expansion of the expansion element beyond a predetermined diameter, which corresponds to a diameter operable to achieve the target final vessel diameter. In some embodiments, the stop may be achieved via selection of materials for the expansion element which is radially compliant in comparison to a fully radially compliant expansion element. This may also be achieved via the use of covers as previously discussed.

It should also be understood from the foregoing that the number of cycles for each treatment program may be selected as desired for a particular treatment to be given. Any of a variety of additional method features may be incorporated into a particular treatment program, including the user and/or system rotating, sliding, or otherwise shifting a relative position of the one or more expansion elements of the system.

The invention of this application has been described above both generically and with regard to specific embodiments. It will be apparent to those skilled in the art that various modifications and variations can be made in the embodiments without departing from the scope of the disclosure. Thus, it is intended that the embodiments cover the modifications and variations of this invention provided they come within the scope of the appended claims and their equivalents.

What is claimed is:

1. A method of treating a vessel having a nominal (starting) diameter at a treatment site in a mammalian body, the method comprising:
   providing an apparatus that includes an expansion element mounted on a catheter, the expansion element configured to enlarge and contract at a first frequency of 0.1 to 10 Hz;
   orienting the expansion element at the treatment site; and
   cycling the expansion element at the treatment site at the first frequency between a first diameter that is greater than the nominal (starting diameter) and a second diameter that is less than the first diameter in a first cycle, wherein the second diameter increases in size during subsequent cycles relative to the second diameter during the first cycle;
   whereby the nominal (starting) diameter of the treatment site is increased following the treatment and removal of the expansion element.

2. The method of claim 1, wherein the expansion element is a drug coated balloon, wherein a result of cycling the drug coated balloon includes increased efficacy of drug delivery to the treatment site.

3. The method of claim 1, wherein the expansion element is cycled according to a frequency configured to treat the treatment site.

4. The method of claim 1, wherein the expansion element is cycled according to a treatment program, wherein the treatment program includes varying strain rate, strain percentages, number of cycles, expansion amplitude, expansion frequency, change in expansion element volume, change in expansion element pressure, or change in expansion element diameter.

5. The method of claim 1, wherein the expansion element has a compliance configured to treat a desired vessel diameter.

6. The method of claim 1, wherein the expansion element is configured to radially expand with an absence of localized shear loading on the vessel.

7. The method of claim 1, wherein the expansion element is longitudinally flexible.

8. The method of claim 1, wherein the expansion element includes a drug coating, scoring elements, cutting elements, topographic features, or a scaffold attached to a balloon.

9. The method of claim 1, wherein the expansion element is cycled at the first frequency using a pressurizing source.

10. A method of treating a tissue site in a body of a patient, the tissue site having a nominal size, the method comprising:
delivering one or more expansion elements of a medical device to the tissue site, the medical device being configured to expand and contract the one or more expansion elements;
operating the medical device according to a treatment program such that the one or more expansion elements are expanded and contracted at a treatment frequency having a value from 0.1 Hz to 10 Hz, the one or more expansion elements being expanded and contracted between a first size and a second size that is greater than the first size through a graduating, cyclic expansion profile including the second size graduating in value from an initial value that is greater than the nominal size and a subsequent value that is greater than the initial value, wherein the second size increases during subsequent cycles relative to the second size during a first cycle; and
removing the one or more expansion elements from the tissue site, whereby the nominal size of the tissue site is increased following removal of the one or more expansion elements.

11. The method of claim 10, wherein the one or more expansion elements include an intraluminal balloon.

12. The method of claim 10, wherein the tissue site is one of a blood vessel, a heart valve, or a respiratory conduit.

13. The method of claim 10, wherein the treatment frequency is varied during the treatment program.

14. The method of claim 10, wherein the treatment frequency is constant during the treatment program.

15. The method of claim 10, wherein the treatment program is carried out using a single expansion element.

16. The method of claim 10, wherein the treatment program includes varying properties of the one or more expansion elements during the treatment program, the properties including a volume, a pressure, or a diameter of the one or more expansion elements.

17. The method of claim 10, wherein the treatment program is configured to carry out, and the method is associated with medical procedures including a sinuplasty, a kyphoplasty, a rhinoplasty, or a skin expansion procedure.

18. The method of claim 10, wherein the one or more expansion elements include a compliant balloon.

19. The method of claim 10, wherein the one or more expansion elements include a non-compliant balloon.

20. The method of claim 10, wherein the medical device is coupled to a pressure modulator that includes a power source connected to a pressurizing source and a controller for controlling the pressurizing source, the pressurizing source being coupled with the one or more expansion elements for pressurizing and de-pressurizing the one or more expansion elements and the controller including a processor for causing the pressurizing source to operate the one or more expansion elements according to the treatment program.

21. The method of claim 20, wherein the power source, the pressurizing source, and the controller are maintained in a housing.

22. The method of claim 21, wherein the housing is configured to be held in a hand of a user.

23. The method of claim 20, wherein the pressure modulator includes a pressurizing source comprising a piston drive, a screw drive, an air compressor, a gas cartridge, a servo motor, a piezo electric motor, or a pressurized fluid reservoir.

24. The method of claim 10, wherein the expansion element comprises scoring features, drug coating, cutting features, controlled topography features, or off axis expansion features.

* * * * *